(12) United States Patent
Battista et al.

(10) Patent No.: US 7,655,670 B2
(45) Date of Patent: Feb. 2, 2010

(54) 3-SPIROCYCLIC INDOLYL DERIVATIVES USEFUL AS ORL-1 RECEPTOR MODULATORS

(75) Inventors: Kathleen A. Battista, Williamstown, NJ (US); Gilles C. Bignan, Bridgewater, NJ (US); Peter J. Connolly, New Providence, NJ (US); Jessica J. Liu, Three Bridges, NJ (US); Steven A. Middleton, Flemington, NJ (US); Michael J. Orsini, Somerset, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 468 days.

(21) Appl. No.: 11/440,731

(22) Filed: May 25, 2006

(65) Prior Publication Data

US 2007/0112016 A1    May 17, 2007

Related U.S. Application Data

(60) Provisional application No. 60/686,857, filed on Jun. 2, 2005.

(51) Int. Cl.
*A61K 31/438*   (2006.01)
*C07D 471/10*   (2006.01)

(52) U.S. Cl. ........................ 514/278; 546/17

(58) Field of Classification Search ................ 514/278; 546/17

See application file for complete search history.

(56) References Cited

U.S. PATENT DOCUMENTS

| 2004/0152707 A1 | 8/2004 | Tulshian et al. |
| 2005/0038060 A1 | 2/2005 | Ando et al. |
| 2006/0079505 A1* | 4/2006 | Makings et al. ........ 514/217.07 |

OTHER PUBLICATIONS

Haynes et al. Stereoselective, Base-Induced Formation of Bicyclo[2.2.1] Heptanones and Bicyclo [3.2.1.] Octanols Formed from the Products of Conjugation Addition of Lithiated Allylic Sulfoxides and Phosphine Oxides to Cyclopean-2-enone. Australian Journal of Chemistry, Sep. 1989, vol. 42, No. 9, pp. 1473-1483, p. 1473, abstract.

* cited by examiner

*Primary Examiner*—Charanjit S Aulakh
(74) *Attorney, Agent, or Firm*—Andrea Jo Kamage

(57) ABSTRACT

The present invention is directed to novel 3-spirocyclic indolyl derivatives, pharmaceutical compositions containing them and their use in the treatment of disorders and conditions modulated by the ORL-1 receptor.

4 Claims, No Drawings

3-SPIROCYCLIC INDOLYL DERIVATIVES USEFUL AS ORL-1 RECEPTOR MODULATORS

CROSS REFERENCE TO RELATED APPLICATIONS

This application claims the benefit of U.S. Provisional Application 60/686,857, filed on Jun. 2, 2005, which is incorporated by reference herein in its entirety.

FIELD OF THE INVENTION

The present invention is directed to novel 3-spirocyclic indolyl derivatives, pharmaceutical compositions containing them and their use in the treatment of disorders and conditions modulated by the ORL-1 receptor. More particularly, the compounds of the present invention are useful in the treatment of disorders and conditions such as anxiety, depression, panic, mania, dementia, bipolar disorder, substance abuse, neuropathic pain, acute pain, chronic pain, migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization.

BACKGROUND OF THE INVENTION

The ORL-1 (orphan opioid receptor) G-protein coupled receptor, also known as the nociceptin receptor, was first reported in 1994, and was discovered based on its homology with the classic delta- (OP-1), mu- (OP-3), and kappa- (OP-2) opioid receptors. The ORL-1 G-protein coupled receptor does not bind opioid ligands with high affinity. The amino acid sequence of ORL-1 is 47% identical to the opioid receptors overall, and 64% identical in the transmembrane domains. (*Nature*, 1995, 377, 532.)

The endogenous ligand of ORL-1, known as nociceptin, a highly basic 17 amino acid peptide, was isolated from tissue extracts in 1995. It was named both nociceptin, because it increased sensitivity to pain when injected into mouse brain, and orphanin FQ (OFQ) because of the terminal phenylalanine (F) and glutamine (Q) residues that flank the peptide on the N- and C-termini respectively. (PCT publication WO97/07212)

Nociceptin binding to ORL-1 receptors causes inhibition of cAMP synthesis, inhibition of voltage-gated calcium channels, and activation of potassium conductance. In vivo, nociceptin produces a variety of pharmacological effects that at times oppose those of the opioids, including hyperalgesia and inhibition of morphine-induced analgesia. Mutant mice lacking nociceptin receptors show better performance in learning and memory tasks. These mutant mice exhibited normal responses to painful stimuli.

The ORL-1 receptor is widely distributed/expressed throughout the human body, including in the brain and spinal cord. In the spinal cord, the ORL-1 receptor exists in both the dorsal and ventral horns, and precursor mRNA has been found in the superficial lamina of the dorsal horn, where primary afferent fibers of nociceptors terminate. Therefore, the ORL-1 has an important role in nociception transmission in the spinal cord. This was confirmed in recent studies wherein nociceptin, when given to mice by i.c.v. (intra-cerebro-ventricular) injection, induced hyperalgesia and decreased locomotor activity. (*Brit. J. Pharmacol.* 2000, 129, 1261.)

We now describe novel small molecule modulators of the ORL-1 receptor, useful for the treatment of disorders and conditions mediated by the ORL-1 receptor, such as anxiety, depression, panic, dementia, mania, bipolar disorder, substance abuse, neuropathic pain, acute pain, chronic pain, migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorders (ADHD), Alzheimer's disease, for improved cognition or memory and for mood stabilization.

SUMMARY OF THE INVENTION

The present invention is directed to compounds of formula (I)

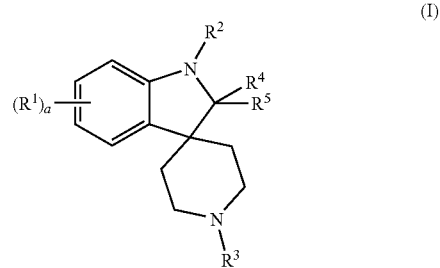

wherein a is an integer from 0 to 2;

$R^1$ is selected from the group consisting of halogen, hydroxy, $C_{1-4}$alkyl, halogenated $C_{1-4}$alkyl, $C_{1-4}$alkoxy, halogenated $C_{1-4}$alkoxy, nitro, cyano, amino, $C_{1-4}$alkylamino and di($C_{1-4}$alkyl)amino;

$R^2$ is selected from the group consisting of hydrogen, —$C_{1-4}$ alkyl, —$C_{1-4}$alkyl-OH, —$C_{1-4}$alkyl-cycloalkyl, —$C_{1-4}$ alkyl-aryl, —$C_{1-4}$alkyl-heterocyclyl, —$C_{1-4}$alkyl-C(O)OH, —$C_{1-4}$alkyl-C(O)O—$C_{1-4}$alkyl, —$C_{1-4}$alkyl-OC(O)—$C_{1-4}$ alkyl, —$CH_2$—$CH(OH)$—$CH_2$—$NR^AR^B$, —$CH_2$—$CH(OH)$—$CH_2$—$S$—$R^C$, —$C_{1-4}$alkyl-oxiranyl and —$C_{1-4}$alkyl-O-tetrahydro-pyran-2-yl;

wherein the cycloalkyl, aryl or heterocyclyl, whether alone or as part of a substituent group is optionally substituted with one to two substituents independently selected from halogen, $C_{1-4}$alkyl, halogenated $C_{1-4}$alkyl, $C_{1-4}$alkoxy, halogenated $C_{1-4}$alkoxy, nitro, cyano, amino, $C_{1-4}$alkylamino or di($C_{1-4}$alkyl)amino;

wherein $R^A$ and $R^B$ are each independently selected from hydrogen, $C_{1-4}$alkyl, $C_{1-4}$alkyl-aryl or —$C_{1-4}$alkyl-heterocyloalkyl, wherein the aryl is optionally substituted with one to two substitutes independently selected from halogen, $C_{1-4}$alkyl, halogenated $C_{1-4}$alkyl, $C_{1-4}$alkoxy or halogenated $C_{1-4}$alkoxy; alternatively, $R^A$ and $R^B$ are taken together with the nitrogen atom to which they are bound to form a 5 to 6 membered, saturated, heterocycloalkyl ring;

wherein $R^C$ is selected from $CH_2$—$CH(CO_2H)$—$NH_{12}$ and $CH_2$—$CH(CO_2H)$—$NH$—$C(O)$—$CH_3$;

$R^3$ is selected from the group consisting of $C_{1-12}$alkyl, cycloalkyl, —$C_{1-4}$alkyl-cycloalkyl, partially unsaturated carbocyclyl, —$C_{1-4}$alkyl-partially unsaturated carbocyclyl, aryl, —$C_{1-4}$alkyl-aryl, heteroaryl, —$C_{1-4}$alkyl-heteroaryl, biphenyl, —$C_{1-4}$alkyl-biphenyl, —$C_{1-4}$alkyl-(phenyl)-(thienyl) and —C(O)O—$C_{1-4}$alkyl;

wherein the cycloalkyl, partially unsaturated carbocyclyl, aryl or heteroaryl, whether alone or as part of a substituent group is optionally substituted with one to two substituents independently selected from halogen, hydroxy, $C_{1-4}$alkyl, halogenated $C_{1-4}$alkyl, $C_{1-4}$alkoxy, halogenated $C_{1-4}$alkoxy, nitro, cyano, amino, $C_{1-4}$alkylamino or di($C_{1-4}$alkyl)amino;

alternatively, $R^3$ is selected from -A-phenyl or -A-cycloalkyl; wherein A is —$C_{1-4}$alkyl-, and wherein the —$C_{1-4}$alkyl- is substituted with one to two oxo groups; and wherein the phenyl or cycloalkyl is optionally substituted with one to two substituents independently selected from halogen, $C_{1-4}$alkyl, halogenated $C_{1-4}$alkyl, $C_{1-4}$alkoxy, halogenated $C_{1-4}$alkoxy, nitro, cyano, amino, $C_{1-4}$alkylamino or di($C_{1-4}$alkyl)amino;

$R^4$ and $R^5$ are each hydrogen or are taken together as =O;

provided that $R^3$ is other than 3-(9-ethyl-9H-carbazolyl)-methyl or 5-(benzo[1,2,5]oxadiazole)-ethyl;

provided further that when a is an integer from 0 to 1, $R^1$ is halogen, $C_{1-4}$alkyl or $C_{1-4}$alkoxy, $R^2$ is hydrogen and $R^4$ and $R^5$ are taken together as =O, then $R^3$ is other than $C_{1-4}$alkyl, t-butoxycarbonyl, phenyl or benzyl;

provided further that when a is an integer from 0 to 1, $R^1$ is halogen, $C_{1-4}$alkyl or nitro, $R^3$ is $C_{1-4}$alkyl or t-butoxycarbonyl, and $R^4$ and $R^5$ are taken together as =O, then $R^2$ is other than benzyl or dimethoxybenzyl;

provided further that when a is 0 ($R^1$ is absent), $R^2$ is methoxy-carbonyl-methyl, and $R^4$ and $R^5$ are taken together as =O, then $R^3$ is other than $C_{1-4}$alkyl or t-butoxycarbonyl;

provided further than when a is an integer from 0 to 1, $R^1$ is $C_{1-4}$alkoxy, $R^2$ is $C_{1-4}$alkyl and $R^4$ and $R^5$ are taken together as =O, then $R^3$ is other than $C_{1-4}$alkyl, —C(O)O—$C_{1-4}$alkyl, benzyl, phenylethyl or pyridyl-ethyl;

provided further that when a is 0 ($R^1$ is absent), $R^2$ is hydrogen or $C_{1-4}$alkyl, $R^4$ is hydrogen and $R^5$ is hydrogen, then $R^3$ is other than 2-hydroxy-cyclohexyl, 2-hydroxy-1,2,3,4-tetrahydronaphthyl, 5-(10,11-dihydro-5H-dibenzo[a,d]cycloheptyl)-propyl- or 4-fluorophenyl-carbonyl-propyl;

provided further that when a is an integer from 0 to 1, $R^1$ is halogen, $R^2$ is hydrogen or $C_{1-4}$alkyl, $R^4$ is hydrogen and $R^5$ is hydrogen, then $R^3$ is other than $C_{1-4}$alkyl, benzyl, phenylethyl or t-butoxycarbonyl;

and pharmaceutically acceptable salts thereof.

The present invention is further directed to processes for the preparation of the compounds of formula (I).

The present invention is further directed to the compounds of formula (XXIV)

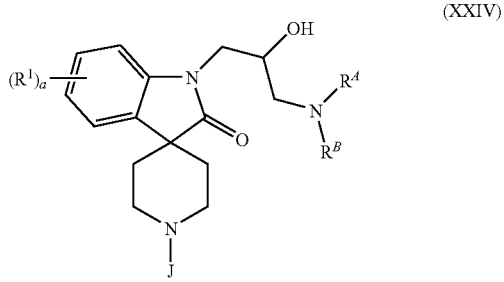

(XXIV)

wherein J is $R^3$ or a suitable nitrogen protecting group. The present invention is further directed to novel processes for the preparation of the compounds of formula (XXIV).

The present invention is further directed to the compounds of formula (XXVI)

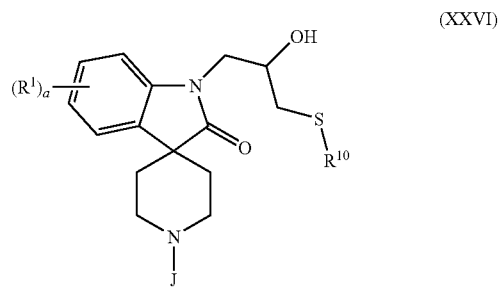

(XXVI)

wherein J is $R^3$ or a suitable nitrogen protecting group. The present invention is further directed to novel processes for the preparation of the compounds of formula (XXVI).

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders and conditions mediated by the ORL-1 receptor in a subject in need thereof comprising administering to the subject a therapeutically effective amount of any of the compounds or pharmaceutical compositions described above.

An example of the invention is a method of treating a condition selected from the group consisting of anxiety, depression, panic, mania, dementia, bipolar disorder, substance abuse, neuropathic pain, acute pain, chronic pain migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization, comprising administering to a subject in need thereof, a therapeutically effective amount of any of the compounds or pharmaceutical compositions described above.

Another example of the invention is the use of any of the compounds described herein in the preparation of a medicament for treating: (a) anxiety, (b) depression, (c) panic, (d) mania, (e) dementia, (f) bipolar disorder, (g) substance abuse (h) neuropathic pain, (i) acute pain, (j) chronic pain, (k) migraine, (l) asthma, (m) cough, (n) psychosis, (o) schizophrenia, (p) epilepsy, (q) hypertension, (r) obesity, (s) eating disorders, (t) cravings, (u) diabetes, (v) cardiac arrhythmia, (w) irritable bowel syndrome, (x) Crohn's disease, (y) urinary incontinence, (z) adrenal disorders, (aa) attention deficit disorder (ADD), (bb) attention deficit hyperactivity disorder (ADHD), (cc) Alzheimer's disease, for (dd) improved cognition, (ee) improved memory and (ff) mood stabilization, in a subject in need of such treatment.

DETAILED DESCRIPTION OF THE INVENTION

The present invention is directed to 3-spirocyclic indolyl derivatives useful for the treatment of disorders and conditions mediated by the ORL-1 receptor. More particularly, the compounds of the present invention are of the general formula (I)

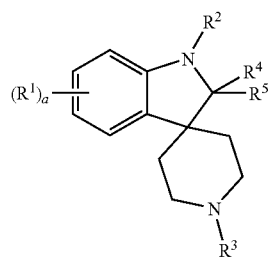

wherein a, $R^1$, $R^2$, $R^3$, $R^4$ and $R^5$ are as herein defined, and pharmaceutically acceptable salts thereof. The compounds of formula (I) are useful in the treatment of disorders mediated by the ORL-1 receptor and/or are intermediates in the synthesis of compounds useful for the treatment of disorders mediated by the ORL-1 receptor. For example, compounds of formula (I) wherein $R^3$ is t-butoxy-carbonyl are useful as intermediates in the synthesis of other compounds of formula (I).

More particularly, ORL-1 mediated disorders include, but are not limited to anxiety, depression, panic, mania, dementia, bipolar disorder, substance abuse, neuropathic pain, acute pain, chronic pain migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization. Preferably, the compounds of formula (I) are useful in the treatment of anxiety, depression, substance abuse, neuropathic pain, acute pain, chronic pain, migraine, cough, hypertension, cardiac arrhythmia, irritable bowel syndrome and Crohn's disease.

In an embodiment of the present invention are compounds of formula (I) which are agonists of the ORL-1 receptor. In a preferred embodiment of the present invention are compounds of formula (I) which are antagonists of the ORL-1 receptor.

The compounds of the present invention are further useful as markers for the ORL-1 receptor. Compounds of formula (I) when used as markers are for example radio-labeled by for example, substituting at least one hydrogen atom with a tritium atom. Other labeling techniques known in the arts can also be used.

In an embodiment of the present invention, a is an integer form 0 to 1. Preferably a is 0. In an embodiment of the present invention, the $R^1$ group is bound at the 8-, 9- or 10-position of the spiro[indoline-3,4'-piperidin]-2-one core.

In an embodiment of the present invention, $R^1$ is selected from the group consisting of halogen, hydroxy, $C_{1-4}$alkyl, halogenated $C_{1-4}$alkyl, $C_{1-4}$alkoxy and halogenated $C_{1-4}$alkoxy. In another embodiment of the present invention, $R^1$ is selected from the group consisting of halogen, hydroxy, $C_{1-4}$alkyl, $C_{1-4}$alkoxy and halogenated $C_{1-4}$alkyl. In another embodiment of the present invention, $R^1$ is selected from the group consisting of fluoro, hydroxy, methyl, isopropyl, methoxy and trifluoromethyl. In another embodiment of the present invention, $R^1$ is selected from the group consisting of 9-fluoro, 8-methyl, 9-methyl, 10-methyl and 9-trifluoromethyl.

Preferably, $R^1$ is selected from the group consisting of 9-fluoro, 8-methyl and 10-methyl. More preferably, $R^1$ is selected from the group consisting of 9-fluoro and 8-methyl.

In an embodiment of the present invention, $R^2$ is selected from the group consisting of hydrogen, —$C_{1-4}$alkyl, —$C_{1-4}$alkyl-OH, —$C_{1-4}$alkyl-$CO_2$H, —$C_{1-4}$alkyl-cycloalkyl, —$C_{1-4}$ alkyl-aryl, —$C_{1-4}$alkyl-C(O)O—$C_{1-4}$alkyl, —$C_{1-4}$alkyl-OC(O)—$C_{1-4}$alkyl, —$C_{1-4}$alkyl-oxiranyl, —$CH_2$—CH(OH)—$CH_2$—$NR^AR^B$, —$CH_2$—CH(OH)—$CH_2$—S—$R^C$, and —$C_{1-4}$alkyl-O-tetrahydro-pyran-2-yl; wherein the cycloalkyl or aryl, whether alone or as part of a substituent group is optionally substituted with one to two substituents independently selected from halogen, $C_{1-4}$alkyl, halogenated $C_{1-4}$alkyl, $C_{1-4}$alkoxy or halogenated $C_{1-4}$alkoxy.

In another embodiment of the present invention, $R^2$ is selected from the group consisting of hydrogen, $C_{1-4}$alkyl, —$C_{1-2}$alkyl-OH, —$C_{1-2}$alkyl-$CO_2$H, —$C_{1-2}$alkyl-cycloalkyl, —$C_{1-2}$alkyl-aryl, $C_{1-2}$alkyl-C(O)O—$C_{1-2}$alkyl, —$C_{1-2}$alkyl-OC(O)—$C_{1-2}$alkyl, —$C_{1-2}$alkyl-oxarinyl, —$CH_2$—CH(OH)—$CH_2$—$NR^AR^B$, —$CH_2$—CH(OH)—$CH_2$—S—$CH_2$—CH($CO_2$H)—NH—C(O)—$CH_3$, and —$C_{1-2}$alkyl-O-tetrahydro-pyran-2-yl; wherein the aryl, whether alone or as part of a substituent group is optionally substituted with a substituent selected from $C_{1-4}$alkoxy.

In another embodiment of the present invention, $R^2$ is selected from the group consisting of hydrogen, methyl, ethyl, n-propyl, hydroxy-ethyl-, carboxy-methyl-, cyclopropyl-methyl-, cyclohexyl-methyl-, benzyl-, 4-methoxy-benzyl-, methoxy-carbonyl-methyl-, methoxy-carbonyl-ethyl-, methyl-carbonyl-oxy-ethyl-, oxarinyl-methyl-, —$CH_2$—CH(OH)—$CH_2$—N(ethyl)(4-methyl-benzyl), —$CH_2$—CH(OH)—$CH_2$—NH—$CH_2CH_2$-(4-morpholinyl), —$CH_2$—CH(OH)—$CH_2$—S—$CH_2$—CH($CO_2$H)—NH—C(O)—$CH_3$, and 2-(tetrahydropyranyl)oxy-ethyl-.

In another embodiment of the present invention, $R^2$ is selected from the group consisting of hydrogen, methyl, hydroxy-ethyl-, cyclohexyl-methyl-, benzyl-, methoxy-carbonyl-methyl-, methyl-carbonyl-oxy-ethyl-, oxarinyl-methyl-, —$CH_2$—CH(OH)—$CH_2$—NH—$CH_2CH_2$-(4-morpholinyl), —$CH_2$—CH(OH)—$CH_2$—N(ethyl)(4-methyl-benzyl) and —$CH_2$—CH(OH)—$CH_2$—S—$CH_2$—CH($CO_2$H)—NH—C(O)—$CH_3$.

Preferably, $R^2$ is selected from the group consisting of methyl, methoxy-carbonyl-methyl-, methyl-carbonyl-oxy-ethyl-, oxarinyl-methyl-, —$CH_2$—CH(OH)—$CH_2$—NH—$CH_2CH_2$-(4-morpholinyl) and —$CH_2$—CH(OH)—$CH_2$—S—$CH_2$—CH($CO_2$H)—NH—C(O)—$CH_3$. More preferably, $R^2$ is selected from the group consisting of methyl and oxarinyl-methyl-.

In an embodiment of the present invention, $R^A$ and $R^B$ are each independently selected from hydrogen, $C_{1-4}$alkyl, —$C_{1-2}$alkyl-aryl or $C_{1-2}$alkyl-(6 membered heterocycloalkyl), wherein the aryl is optionally substituted with one to two substitutes independently selected from halogen, $C_{1-4}$alkyl, halogenated $C_{1-4}$alkyl, $C_{1-4}$alkoxy or halogenated $C_{1-4}$alkoxy.

In another embodiment of the present invention, $R^A$ and $R^B$ are each independently selected from $C_{1-2}$alkyl, —$C_{1-2}$alkyl-phenyl or —$C_{1-2}$alkyl-(6 membered saturated heterocycloalkyl), wherein the phenyl is optionally substituted with a $C_{1-4}$alkyl. Preferably, $R^A$ and $R^B$ are each independently selected from hydrogen, ethyl, 4-methyl-benzyl and 4-morpholinyl-ethyl-.

In an embodiment of the present invention, $R^A$ and $R^B$ are taken together with the nitrogen atom to which they are bound to form a 5 to 6 membered, saturated, heterocycloalkyl ring. In another embodiment of the present invention, $R^A$ and $R^B$ are taken together with the nitrogen atom to which they are bound to form a 6-membered, saturated heterocycloalkyl ring.

In an embodiment of the present invention, $R^C$ is selected from —$CH_2$—CH($CO_2$H)—$NH_2$ and —$CH_2$—CH($CO_2$H)—NH—C(O)—$CH_3$.

In an embodiment of the present invention, $R^3$ is selected from the group consisting of $C_{1-12}$alkyl, cycloalkyl, —$C_{1-4}$alkyl-cycloalkyl, partially unsaturated carbocyclyl, —$C_{1-4}$alkyl-partially unsaturated carbocyclyl, aryl, —$C_{1-4}$alkyl-aryl, biphenyl, —$C_{1-4}$alkyl-biphenyl, —$C_{1-4}$alkyl-(phenyl)-(thienyl) and —C(O)O—$C_{1-4}$alkyl; wherein the cycloalkyl, partially unsaturated carbocyclyl or aryl, whether alone or as part of a substituent group is optionally substituted with one to two substituents independently selected from halogen, hydroxy, $C_{1-4}$alkyl, halogenated $C_{1-4}$alkyl, $C_{1-4}$alkoxy or halogenated $C_{1-4}$alkoxy.

In another embodiment of the present invention, $R^3$ is selected from the group consisting of $C_{1-12}$alkyl, partially unsaturated carbocyclyl, —$C_{1-2}$alkyl-cycloalkyl, $C_{1-2}$alkyl-aryl, —$C_{1-2}$alkyl-biphenyl, —$C_{1-2}$alkyl-(phenyl)-(thienyl) and —C(O)O—$C_{1-4}$alkyl; wherein the cycloalkyl or aryl, whether alone or as part of a substituent group is optionally substituted with a group selected from halogen, $C_{1-4}$alkyl or fluorinated $C_{1-4}$alkyl.

In another embodiment of the present invention, $R^3$ is selected from the group consisting of methyl, n-hexyl, 5-undecyl, 2-decahydronaphthyl, cyclopropyl-methyl-, cyclohexyl-methyl-, t-butyl-cyclohexyl-methyl-, cycloheptyl-methyl-, cyclooctyl-methyl-, cyclododecyl-methyl-, 1-acenaphthyl, 2-(1,2,3,4-tetrahydronaphthyl), 1-naphthyl-methyl, 2-naphthyl-phenyl, phenyl-ethyl-, 4-chlorobenzyl-, 3-trifluoromethyl-benzyl-, 4-trifluoromethyl-benzyl-, 1-naphthyl-methyl-, 4-biphenyl-methyl-, 2-(3-thienyl)-benzyl- and t-butoxy-carbonyl-.

In another embodiment of the present invention, $R^3$ is selected from the group consisting of n-hexyl, 4-t-butyl-cyclohexyl-methyl-, cycloheptyl-methyl-, cyclooctyl-methyl-, 2-decahydronaphthyl, 1-acenaphthyl, 1-naphthyl-methyl, 2-naphthyl-methyl-, 3-trifluoromethyl-benzyl-, 4-chlorobenzyl-, and t-butoxy-carbonyl.

Preferably, $R^3$ is selected from the group consisting of 4-t-butyl-cyclohexyl-methyl-, cyclooctyl-methyl-, 2-naphthyl-methyl- and 3-trifluoromethyl-benzyl-. More preferably, $R^3$ is cyclooctyl-methyl-.

In an embodiment of the present invention, $R^3$ is selected from the group consisting of cycloalkyl, —$C_{1-4}$alkyl-cycloalkyl, partially unsaturated carbocyclyl, —$C_{1-4}$alkyl-partially unsaturated carbocyclyl, aryl, —$C_{1-4}$alkyl-aryl, heteroaryl and —$C_{1-4}$alkyl-heteroaryl.

In another embodiment of the present invention $R^3$ is selected from the group consisting of —$C_{1-4}$alkyl-cycloalkyl, —$C_{1-4}$alkyl-partially unsaturated carbocyclyl, —$C_{1-4}$alkyl-aryl and —$C_{1-4}$alkyl-heteroaryl.

In yet another embodiment of the present invention $R^3$ is selected from the group consisting of cycloalkyl, —$C_{1-4}$alkyl-cycloalkyl, partially unsaturated carbocyclyl, —$C_{1-4}$alkyl-partially unsaturated carbocyclyl, aryl and —$C_{1-4}$alkyl-aryl. In yet another embodiment of the present invention $R^3$ is selected from the group consisting of heteroaryl and —$C_{1-4}$alkyl-heteroaryl.

In an embodiment of the present invention, $R^3$ is selected from -A- phenyl or -A-cycloalkyl; wherein A is —$C_{1-14}$alkyl-, wherein the —$C_{1-4}$alkyl- is substituted with one to two oxo groups; and wherein the phenyl or cycloalkyl is optionally substituted with one to two substituents independently selected from halogen, $C_{1-4}$alkyl, halogenated $C_{1-4}$alkyl, $C_{1-4}$alkoxy or halogenated $C_{1-4}$alkoxy.

In another embodiment of the present invention, $R^3$ is selected from -A-phenyl or -A-cycloalkyl; wherein A is —$C_{1-4}$alkyl-, wherein the —$C_{1-4}$alkyl- is substituted with one to two oxo groups; and wherein the phenyl or cycloalkyl is optionally substituted with a substituent selected from $C_{1-4}$alkoxy.

Preferably, A is selected from the group consisting of —C(O)— and C(O)—CH$_2$CH$_2$—C(O)—. Preferably, $R^3$ is selected from the group consisting of 4-methoxy-cyclohexyl-carbonyl- and phenyl-carbonyl-ethyl-carbonyl-.

In an embodiment of the present invention $R^4$ and $R^5$ are each hydrogen. Preferably $R^4$ and $R^5$ are taken together as =O (oxo).

In an embodiment of the present invention, $R^2$ is other than hydrogen or $C_{1-4}$alkyl. In an embodiment of the present invention, $R^3$ is other than $C_{1-4}$alkyl or —C(O)O—$C_{1-4}$alkyl. In another embodiment of the present invention, $R^3$ is other than phenyl, benzyl or phenylethyl. In another embodiment of the present invention $R^3$ is other than t-butoxycarbonyl. In yet another embodiment of the present invention $R^3$ is other than -A-phenyl or -A-cycloalkyl.

Additional embodiments of the present invention, include those wherein the substituents selected for one or more of the variables defined herein (i.e. a, $R^1$, $R^2$, $R^3$, $R^4$ and $R^5$) are independently selected to be any individual substituent or any subset of substituents selected from the complete list as defined herein.

In another embodiment of the present invention is any single compound or subset of compounds selected from the representative compounds listed in tables 1-2, below.

Representative compounds of the present invention are as listed in Table 1, below. Unless otherwise noted, wherein a stereogenic center is present in the listed compound, the compound was prepared as a mixture of stereo-configurations. Where a stereogenic center is present, the S*- and R* designations are intended to indicate that the exact stereo-configuration of the center has not been determined.

TABLE 1

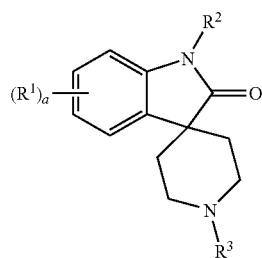

| Compound # | $(R^1)_a$ | $R^2$ | $R^3$ |
|---|---|---|---|
| 1 | a = 0 | methoxy-carbonyl-methyl- | cycloheptyl-methyl- |

TABLE 1-continued

| Compound # | (R¹)ₐ | R² | R³ |
| --- | --- | --- | --- |
| 2 | a = 0 | 2-(tetrahydro-pyranyl)oxy-ethyl- | methyl |
| 3 | a = 0 | cyclohexyl-methyl- | cyclooctyl-methyl- |
| 4 | a = 0 | cyclohexyl-methyl- | 1-acenaphthyl |
| 5 | 10-methoxy | cyclopropyl-methyl- | cyclooctyl-methyl- |
| 6 | 9-isopropyl | methyl | t-butoxy-carbonyl- |
| 7 | 9-isopropyl | methyl | cyclooctyl-methyl- |
| 8 | 9-trifluoromethyl | methyl | cyclooctyl-methyl- |
| 9 | 9-fluoro | methyl | cyclooctyl-methyl- |
| 10 | 9-fluoro | methyl | t-butoxy-carbonyl- |
| 11 | a = 0 | methoxy-carbonyl-methyl- | 4-trifluoromethyl-benzyl- |
| 12 | a = 0 | methoxy-carbonyl-methyl- | 3-trifluoromethyl-benzyl- |
| 13 | a = 0 | methoxy-carbonyl-methyl- | 4-biphenyl-methyl- |
| 14 | 9-trifluoromethyl | methyl | t-butoxy-carbonyl- |
| 15 | a = 0 | methoxy-carbonyl-methyl- | 2-decahydronaphthyl |
| 16 | a = 0 | —CH₂—CH(OH)—CH₂—S—CH₂—CH(CO₂H)—NH—C(O)—CH₃ | cyclooctyl-methyl- |
| 17 | 9-isopropyl | n-propyl | cyclooctyl-methyl- |
| 18 | a = 0 | hydrogen | cyclooctyl-methyl- |
| 19 | 10-hydroxy | methyl | cyclooctyl-methyl- |
| 20 | a = 0 | hydroxy-ethyl- | cyclooctyl-methyl- |
| 21 | a = 0 | 4-methoxy-benzyl- | cyclooctyl-methyl- |
| 22 | a = 0 | methoxy-carbonyl-methyl- | 4-methoxy-cyclohexyl-carbonyl- |
| 23 | a = 0 | methoxy-carbonyl-methyl- | cyclopropyl-methyl- |
| 24 | a = 0 | methoxy-carbonyl-methyl- | cyclohexyl-methyl- |
| 25 | a = 0 | methoxy-carbonyl-methyl- | 2-(1,2,3,4-tetrahydro-naphthyl) |
| 26 | a = 0 | methoxy-carbonyl methyl- | n-hexyl |
| 27 | a = 0 | methoxy-carbonyl-methyl- | cyclododecyl-methyl- |
| 28 | a = 0 | methoxy-carbonyl-methyl- | 5-undecyl |
| 29 | a = 0 | methoxy-carbonyl-methyl- | 4-t-butyl-cyclohexyl-methyl- |
| 30 | a = 0 | methoxy-carbonyl-methyl- | 1-acenaphthyl |
| 31 | a = 0 | methoxy-carbonyl-methyl- | phenyl-carbonyl-ethyl-carbonyl- |
| 32 | a = 0 | methoxy-carbonyl-methyl- | 2-naphthyl-methyl- |
| 33 | 9-isopropyl | n-propyl | t-butoxy-carbonyl- |
| 34 | 10-methoxy | methyl | t-butoxy-carbonyl- |
| 35 | 10-methoxy | methyl | cyclooctyl-methyl- |
| 36 | a = 0 | hydrogen | methyl |
| 37 | a = 0 | methoxy-carbonyl-methyl- | phenyl-ethyl- |
| 38 | 10-methoxy | ethyl | t-butoxy-carbonyl- |
| 39 | a = 0 | methoxy-carbonyl-methyl- | 4-chloro-benzyl- |
| 40 | a = 0 | methoxy-carbonyl-methyl- | 2-(3-thienyl)-benzyl- |
| 41 | a = 0 | carboxy-methyl- | cyclooctyl-methyl- |
| 42 | a = 0 | methoxy-carbonyl-methyl- | cyclooctyl-methyl- |

TABLE 1-continued

| Compound # | $(R^1)_a$ | $R^2$ | $R^3$ |
|---|---|---|---|
| 43 | a = 0 | methoxy-carbonyl-methyl- | 1-naphthyl-methyl- |
| 44 | a = 0 | benzyl | cyclooctyl-methyl- |
| 45 | a = 0 | methyl | cyclooctyl-methyl- |
| 46 | a = 0 | methyl-carbonyl-oxy-ethyl- | cyclooctyl-methyl- |
| 47 | a = 0 | 2-(tetrahydro-pyranyl)oxy-ethyl- | t-butoxy-carbonyl- |
| 48 | a = 0 | 4-methoxy-benzyl- | t-butoxy-carbonyl- |
| 49 | a = 0 | benzyl | t-butoxy-carbonyl- |
| 50 | a = 0 | methyl | t-butoxy-carbonyl- |
| 51 | a = 0 | cyclohexyl-methyl- | t-butoxy-carbonyl- |
| 52 | a = 0 | hydroxy-ethyl- | t-butoxy-carbonyl- |
| 53 | a = 0 | methyl-carbonyl-oxy-ethyl- | t-butoxy-carbonyl- |
| 54 | 10-methoxy | cyclopropyl-methyl- | t-butoxy-carbonyl- |
| 55 | 10-methoxy | ethyl | cyclooctyl-methyl- |
| 56 | 9-methyl | methyl | t-butoxy-carbonyl- |
| 57 | 9-methyl | methyl | cyclooctyl-methyl- |
| 58 | 10-methyl | methyl | cyclooctyl-methyl- |
| 59 | 8-methyl | methyl | cyclooctyl-methyl- |
| 60 | a = 0 | oxiranyl-methyl- | cyclooctyl-methyl- |
| 61 | a = 0 | —$CH_2$—CH(OH)—$CH_2$—NH—$CH_2CH_2$—(4-morpholinyl) | cyclooctyl-methyl- |
| 62 | a = 0 | —$CH_2$—CH(OH)—$CH_2$—N($CH_2CH_3$)—(4-methyl-benzyl) | cyclooctyl-methyl- |

Additional representative compounds of the present invention are as in Table 2.

TABLE 2

Compound #63

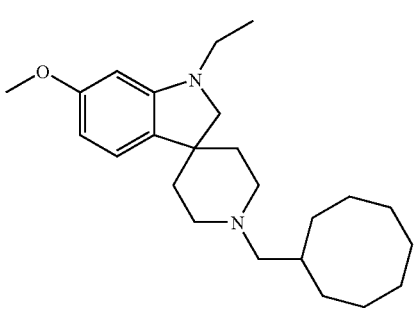

As used herein, "halogen" shall mean chlorine, bromine, fluorine and iodine; preferably chlorine, bromine or fluorine, more preferably, fluorine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, n-pentyl, n-heptyl, 5-undecyl, and the like. Unless otherwise noted, "$C_{1-4}$" when used with alkyl (as in $C_{1-4}$alkyl) shall mean a carbon chain composition of 1-4 carbon atoms, for example, methyl, ethyl, n-propyl, isopropyl, n-butyl, isobutyl, sec-butyl and tert-butyl. Similarly, "$C_{1-12}$" when used with alkyl (as in $C_{1-12}$alkyl) shall mean a carbon chain composition of 1-12 carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include, but are not limited to, —$CF_3$, —$CH_2$—$CF_3$, —$CF_2$—$CF_2$—$CF_2$—$CF_3$, and the like. Similarly, the term "fluorinated $C_{1-4}$alkyl" shall mean any $C_{1-4}$alkyl group as defined above substituted with at least one fluoro atom, preferably one to three fluoro atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{1-4}$" when used with alkoxy (as in $C_{1-4}$alkoxy) shall mean a carbon chain composition of 1-4 carbon atoms, for example, methoxy, ethoxy, n-propoxy, and the like.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include, but are not limited to, —$OCF_3$, —$OCH_2$—

—CF₃, —OCF₂—CF₂—CF₂—CF₃, and the like. Similarly, the term "fluorinated C₁₋₄alkoxy" shall mean any C₁₋₄alkoxy group as defined above substituted with at least one fluoro atom, preferably one to three fluoro atoms.

As used herein, the term "C₁₋₄alkoxycarbonyl" shall mean a group of the formula —C(O)—O—C₁₋₄alkyl. For example, t-butoxycarbonyl shall mean a substituent group of the formula —C(O)—O—C(CH₃)₃.

As used herein, unless otherwise noted, "aryl" shall refer to unsubstituted carbocylic aromatic groups such as phenyl, naphthyl, and the like; preferably phenyl or naphthyl, more preferably, phenyl.

As used herein, unless otherwise noted, the term "cycloalkyl" shall mean any stable monocyclic, bicyclic, polycyclic or bridged, saturated ring system; preferably a monocyclic or bicyclic saturated ring system. Suitable examples include, but are not limited to cyclopropyl, cyclobutyl, cyclopentyl, cyclohexyl, cycloheptyl, cyclooctyl, decahydronaphthyl, cyclododecyl, and the like.

As used herein, unless otherwise noted, the term "partially unsaturated carbocyclyl" shall mean any stable monocyclic, bicyclic, polycyclic or bridged ring system (preferably a monocyclic or bicyclic ring system), wherein the ring system contains at least one unsaturated bond. The partially unsaturated carbocycle may further be benzo-fused and/or partially aromatic. Suitable examples include, but are not limited to, 1-acenaphthenyl, cyclohexenyl, 1,2,3,4-tetrahydronaphthyl, and the like.

As used herein, unless otherwise noted, the term "carbocyclyl" shall mean any cycloalkyl, partially unsaturated carbocyclyl or aryl, as herein defined.

As used herein, unless otherwise noted, "heteroaryl" shall mean any monocyclic, bicyclic, bridged or polycyclic aromatic ring structure (preferably a monocyclic or bicyclic aromatic ring structure) containing at least one heteroatom selected from the group consisting of O, N and S, optionally containing one or more, preferably one to four, more preferably, one to two, additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like. Preferred heteroaryl groups include quinazolinyl, isoquinolinyl and thienyl.

As used herein, the term "heterocycloalkyl" shall mean any monocyclic, bicyclic, bridged or polycyclic saturated, partially unsaturated or partially aromatic ring structure (preferably a monocyclic or bicyclic ring structure) containing at least one heteroatom selected from the group consisting of O, N and S, optionally containing one or more, preferably, one to four, more preferably, one to two, additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like. Preferred heterocycloalkyl groups include tetrahydropyranyl, morpholinyl, piperidinyl and oxiranyl.

As used herein, unless otherwise noted, the term "heterocyclyl" shall mean any heteroaryl or heterocycloalkyl, as herein defined.

When a particular group is "substituted" (e.g., cycloalkyl, aryl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, CH₂=CH—CH₂—, and the like; amides—groups of the formula —C(O)—R' wherein R' is for example methyl, phenyl, trifluoromethyl, and the like; N-sulfonyl derivatives—groups of the formula —SO₂—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenylC₁₋₆alkylaminocarbonylC₁-C₆alkyl-" substituent refers to a group of the formula

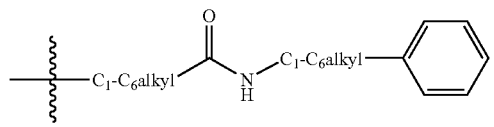

Unless otherwise noted, substituent groups on the compounds of formula (I) are numbered clockwise around the core beginning with the indolyl nitrogen atom, as shown below Abbreviations used in the specification, particularly the Schemes and Examples, are as follows:
BINAP=2,2'-Bis(diphenylphosphino)-1,1'-binaphthyl
BOC or Boc=Tert-butoxy-carbonyl-
CBz=Benzyloxycarbonyl ($C_6H_5$—$CH_2$—O—C(O)—)
DCC=N,N-dicyclohexylcarbodiimide.
DCM=Dichloromethane
DIPEA or DIEA=Diisopropylethylamine
DMF=N,N-Dimethylformamide
DMSO=Dimethylsulfoxide
EGTA=Ethylene glycol-O,O'-bis(2-aminoethyl)-N,N,N',N'-tetracacetic acid
$Et_3N$=Triethylamine
Fmoc=9-Fluorenylmethoxycarbonyl
HATU=O-(7-Azabenzotriazol-1-yl)-N,N,N",N"-Tetramethyl Uronium Hexafluorophosphate
HOBT=1-Hydroxybenzotriazole
KO-t-Bu=Potassium Tert-butoxide
LAH=Lithium aluminum hydride
LiHMDS=Lithium bis(trimethylsilyl)amide
NaHMDS=Sodium bis(trimethylsilyl)amide
$NaBH(OAc)_3$=Sodium tricaetoxyborohydride
NMP=N-methyl-2-pyrrolidinone
$Pd(dba)_2$=Palladium Bis(dibenzylidene acetone)
$Pd_2(OAc)_2$=Palladium(II)acetate
$Pd_2(dba)_3$=Tris(dibenzylidene acetone)dipalladium(0)
$P(t-Bu)_3$=Tri-t-butyl phosphine
t-BuONa or NaO-t-Bu=Sodium tert-butoxide
TEA=Triethylamine
TFA=Trifluoroacetic acid
THF=Tetrahydrofuran
Tris HCl or Tris-Cl=Tris[hydroxymethyl]aminomethyl hydrochloride The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The compounds of the present invention may be prepared according to the processes as described in more detail in the Schemes and Examples which follow herein.

Compounds of formula (I) wherein $R^4$ and $R^5$ are taken together as =O may be prepared according to the process outlined in Scheme 1.

Accordingly, a suitably substituted compound of formula (V), wherein Q is first a suitable leaving group such as Cl, Br, I, and the like, a known compound or compound prepared by known methods, is reacted with a suitably substituted activated compound of formula (VI), wherein X is a second suitable leaving group such as Cl, anhydride, and the like, and wherein $Pg^1$ is a suitable nitrogen protecting group such as t-butoxycarbonyl (BOC), CBz, Fmoc, benzhydryl, triphenylmethyl, 4-methoxybenzyl, benzoyl, and the like, a known compound or compound prepared by known methods, in the presence of a base such as NaH, KH, sodium trimethylsilylamide, TEA, DIPEA, and the like, wherein the base is present in amount equal to or greater than about one molar equivalent, in an organic solvent such as THF, NMP, DMF, DCM, and the like, to yield the corresponding compound of formula (VII).

Alternatively, the compound of formula (V) is reacted with the compound of formula (VI) in the presence of a coupling agent such as HATU, HOBT, DCC, and the like.

The compound of formula (VII) is reacted with a suitably substituted compound of formula (VIII), wherein Y is a third suitable leaving group such as Cl, Br, I, tosylate, mesylate, and the like, a known compound or compound prepared by known methods, in the presence of a base such as NaH, KH, sodium trimethylsilylamide, NaHMDS, LiHMDS, and the like, wherein the base is present in amount equal to or greater than about one molar equivalent, in an organic solvent such as THF, NMP, DMF, and the like, to yield the corresponding compound of formula (IX).

The compound of formula (IX) is reacted in the presence of a catalyst such as $Pd(OAc)_2$, $Pd_2(dba)_3$, and the like, in the presence of a phosphine ligand such as BINAP, $P(tBu)_3$, and the like, in the presence of a base such as $Na_2CO_3$, tBuONa, and the like, in an organic solvent such as toluene, dioxane, and the like, preferably at an elevated temperature in the range of about 30° C. to about 120° C., to yield the corresponding compound of formula (X).

The compound of formula (X) is de-protected by known methods, to yield the corresponding compound of formula (XI). For example, wherein the $Pg^1$ protecting group is Boc, the compound of formula (X) is reacted with an acid such as TFA, HCl, and the like.

The compound of formula (XI) is reacted with a suitably substituted compound of formula (XII), wherein Z is a fourth suitable leaving group such as Cl, Br, I, tosylate, mesylate, and the like, a known compound or compound prepared by known methods, in the presence of a base such as TEA, DIPEA, pyridine, $Na_2CO_3$, $K_2CO_3$, and the like, wherein the base is present in an amount equal to or greater than about one molar equivalent, in an organic solvent such as DMF, DMSO, NMP, and the like, to yield the corresponding compound of formula (Ia).

Alternatively, the compound of formula (XI) is reacted with a suitably substituted compound of formula (XII), wherein Z is an aldehyde (—CHO), a known compound or compound prepared by known methods, in the presence of a reducing agent such as $NaBH(OAc)_3$, $Na(BH_3)CN$, and the like, to yield the corresponding compound of formula (Ia).

Alternatively still, the compound of formula (XI) is reacted with a suitably substituted compound of formula (XII), wherein Z is an acid (—$CO_2H$) or acid chloride (—C(O)Cl), a known compound or compound prepared by known methods, in the presence of a coupling agent such as HATU, DCC, and the like, to yield the corresponding compound of formula (Ia).

Compounds of formula (I) wherein $R^4$ and $R^5$ are each hydrogen may be prepared from the corresponding compound of formula (XI) wherein $R^4$ and $R^5$ are taken together as =O, according to the process outlined in Scheme 2.

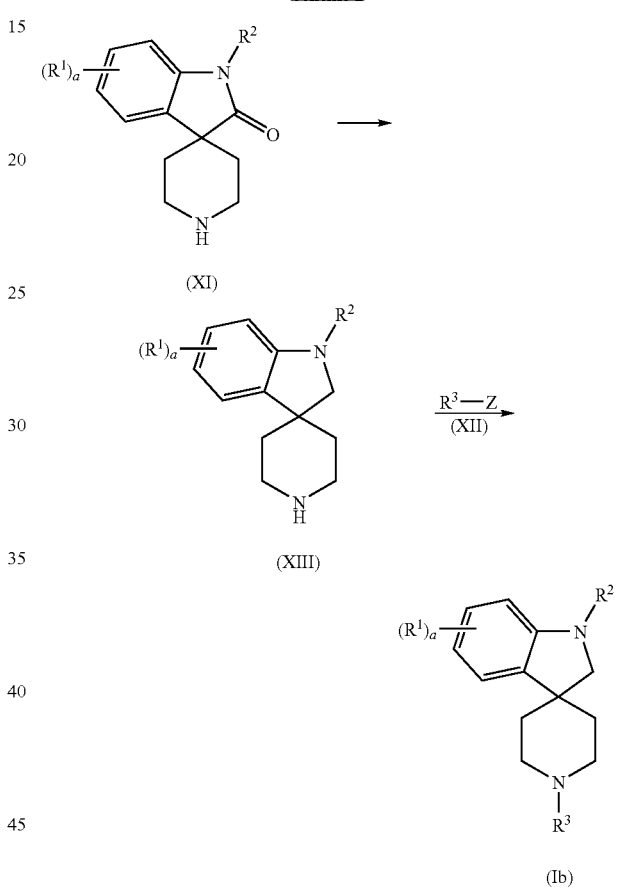

Accordingly, a suitably substituted compound of formula (XI) is reacted with a suitable reducing agent such LAH, LiHDMS, NaHDMS, and the like, in an organic solvent such as DMF, THF, and the like, preferably at a temperature in the range of about 0° C. to about 80° C., to yield the corresponding compound of formula (XIII).

The compound of formula (XIII) is then reacted with a suitably substituted compound of formula (XII), as described in Scheme 1, above, to yield the corresponding compound of formula (Ib).

Compounds of formula (I) wherein $R^2$ is selected from —$CH_2$—CH(OH)—$CH_2$—$NR^AR^B$ or —$CH_2$—CH(OH)—$CH_2$—S—$CH_2$—$CH(CO_2H)$—NH—C(O)—$CH_3$ may be prepared according to the process outlined in Scheme 3.

Scheme 3

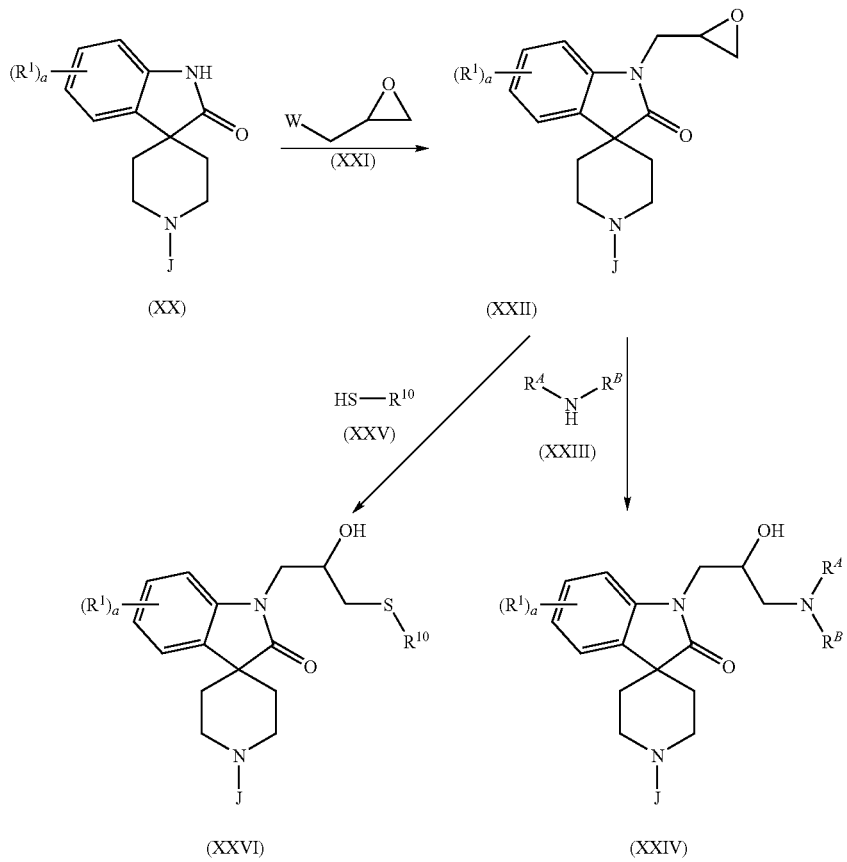

Accordingly, a suitably substituted compound of formula (XX), wherein J is $R^3$ or $Pg^2$, a suitable nitrogen protecting group, a known compound or compound prepared by known methods, is reacted with a compound of formula (XXI), wherein W is a suitable leaving group such as Cl, Br, I, tosylate, mesylate, and the like, a known compound or compound prepared by known methods, in the presence of a base such as NaH, KO-t-Bu, $K_2CO_3$, NaHMDS, LiHMDS, and the like, in an organic solvent such as NMP, DMF, THF, and the like, to yield the corresponding compound of formula (XXII).

The compound of formula (XXII) is reacted with a suitably substituted compound of formula (XXIII), a known compound or compound prepared by known methods, in an organic solvent such as methanol, ethanol, isopropanol, acetonitrile, THF, and the like, to yield the corresponding compound of formula (XXIV).

One skilled in the art will recognize that wherein the compound of formula (XXIV), J is $R^3$, then the process described above yields the corresponding compound of formula (I). One skilled in the art will further recognize that wherein the compound of formula (XXIV), J is $Pg^2$ (a suitable nitrogen protecting group), the compound of formula (XXIV) may be further de-protected and reacted with a suitably substituted compound of formula (XII), as described in Scheme 1 above, to yield the corresponding compound of formula (I).

Alternatively, the compound of formula (XXII) is reacted with a suitably substituted compound of formula (XXV), a known compound or compound prepared by known methods, in the presence of a base such as TEA, DIPEA, pyridine, and the like, in a protic solvent such as methanol, ethanol, NMP, and the like, preferably at a temperature in the range of from about 50° C. to about 100° C., to yield the corresponding compound of formula (XXVI).

One skilled in the art will recognize that wherein the compound of formula (XXVI), J is $R^3$, then the process described above yields the corresponding compound of formula (I). One skilled in the art will further recognize that wherein the compound of formula (XXVI), J is $Pg^2$ (a suitable nitrogen protecting group), the compound of formula (XXVI) may be further de-protected and reacted with a suitably substituted compound of formula (XII), as described in Scheme 1 above, to yield the corresponding compound of formula (I).

One skilled in the art will recognize that wherein any of the processes as described herein, more than one suitable leaving group is present in one or more reagents and/or intermediates, each leaving group is independently selected from a list of suitable leaving groups and as such may be the same or different. One skilled in the art will further recognize that depending on the reaction step, conditions and intermediates, the list of suitable leaving groups for reagents and/or intermediate may vary, and further that the identity of suitable leaving groups for said reagents and/or intermediates would be readily determined by one of skill in the art.

Where the processes for the preparation of the compounds according to the invention give rise to mixture of stereoisomers, these isomers may be separated by conventional techniques such as preparative chromatography.

The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

One skilled in the art will recognize further that wherein a reaction step as described herein may be carried out in a variety of solvents or solvent systems, said reaction step may also be carried out in a mixture of the suitable solvents or solvent systems.

Where the compounds according to this invention have at least one chiral center, they may accordingly exist as enantiomers. Where the compounds possess two or more chiral centers, they may additionally exist as diastereomers. It is to be understood that all such isomers and mixtures thereof (e.g. racemates, etc.) are encompassed within the scope of the present invention. Preferably, wherein a compound of the present invention is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein a compound of the present invention is present as a diastereomer, the diastereomer is present in a diastereomeric excess of greater than or equal to about 80%, more preferably, in a diastereomeric excess of greater than or equal to about 90%, more preferably still, in a diastereomeric excess of greater than or equal to about 95%, more preferably still, in a diastereomeric excess of greater than or equal to about 98%, most preferably, in a diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluene-sulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2- hydroxyethyl)-pyrrolidine, secondary amine, sodium hydroxide, triethanolamine, tromethamine and zinc hydroxide.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-500 mg and may be given at a dosage of from about 0.01-10.0 mg/kg/day, preferably from about 0.1-5.0 mg/kg/day, more preferably from about 0.5-5.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by the ORL-1 receptor described in the present invention may also be carried out using a pharmaceutical composition comprising any of the compounds as defined herein and a pharmaceutically acceptable carrier. The pharmaceutical composition may contain between about 0.1 mg and 500 mg, preferably about 10 to 250 mg, more preferably between about 10 mg and 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders mediated by the ORL-1 receptor is required.

The daily dosage of the products may be varied over a wide range from 0.01 to 500 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.01 to about 10.0 mg/kg of body weight per day, more preferably, from about 0.1 to about 5.0 mg/kg of body weight per day, more preferably still, from about 0.5 to about 5.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

4-(2-Bromo-phenylcarbamoyl)-piperidine-1-carboxylic acid tert-butyl ester

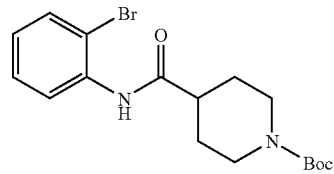

Piperidine-1,4-dicarboxylic acid mono-tert-butyl ester (10.0 g, 43.61 mmol) was dissolved in dry methylene chloride (62 mL) and dry pyridine (9.0 mL). To the reaction mixture was then added thionyl chloride (6.23 g, 52.34 mmol) under nitrogen atmosphere and the reaction mixture was stirred at room temperature for 30 minutes. To the reaction mixture was then added successively, under nitrogen atmosphere, 2-bromo-aniline (8.25 g, 47.98 mmol), dry triethylamine (15.45 g, 0.152 mol), dry methylene chloride (76 mL), 4-(dimethylamino)pyridine (0.53 g, 4.36 mmol) and the reaction mixture was stirred at room temperature for 24 hours. The reaction mixture was then partitioned with aqueous 2N HCl and tert-butyl methyl ether. The organic layer was washed with aqueous 2N HCl, aqueous $NaHCO_3$, brine, dried with $Na_2SO_4$, filtered and the solvent evaporated in vacuo to yield a crude oil. The crude oil was recrystallized from ethyl acetate to yield the title compound as a solid.

$^1$H NMR (300 MHz, DMSO) δ 9.45 (1H, s), 7.65 (1H, m), 7.54 (1H, m), 7.35 (1H, m), 7.15 (1H, m), 3.99 (2H, m), 2.86-2.76 (2H, m), 2.70-2.58 (1H, m), 1.83 (2H, m), 1.58-1.41 (2H, m), 1.42 (9H, s)

MS (ES$^+$) m/z 407.0 (MNa)$^+$

EXAMPLE 2

4-(2-Bromo-5-methoxy-phenylcarbamoyl)-piperidine-1-carboxylic acid tert-butyl ester

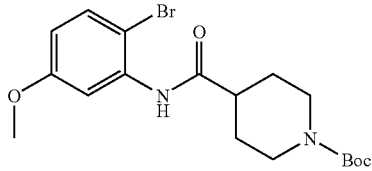

Piperidine-1,4-dicarboxylic acid mono-tert-butyl ester (2.9 g, 12.68 mmol) was dissolved in dry methylene chloride (19 mL) and dry pyridine (2.61 mL). To the reaction mixture was then added thionyl chloride (1.81 g, 15.22 mmol) under nitrogen atmosphere and the reaction mixture was stirred at room temperature for 30 minutes. To the reaction mixture was then added successively, under nitrogen atmosphere, 2-bromo-5-methoxy-phenylamine (2.82 g, 13.95 mmol), dry triethylamine (4.49 g, 44.40 mmol), dry methylene chloride (23 mL), 4-(dimethylamino)pyridine (0.15 g, 1.26 mmol) and the reaction mixture was stirred at room temperature for 24 hours. The reaction mixture was then partitioned with aqueous 2N HCl and tert-butyl methyl ether. The organic layer was washed with aqueous 2N HCl, aqueous NaHCO$_3$, brine, dried with Na$_2$SO$_4$, filtered and the solvent evaporated in vacuo to yield a crude oil. The crude oil was purified via flash chromatography (25% ethyl acetate/hexanes) to yield the title compound as a solid.

$^1$H NMR (300 MHz, CDCl$_3$) δ 8.09 (1H, bs), 7.71 (1H, bs), 7.39 (1H, d, J=8.9 Hz), 6.59-6.55 (1H, m), 4.19-4.11 (2H, m), 3.80 (3H, s), 2.86-2.78 (2H, m), 2.50-2.42 (1H, m), 1.98-1.94 (2H, m), 1.81-1.68 (2H, m), 1.47 (9H, s) MS (ES$^+$) m/z 435.1 (M+H)$^+$

EXAMPLE 3

4-(5-Benzyloxy-2-bromo-phenylcarbamoyl)-piperidine-1-carboxylic acid tert-butyl ester

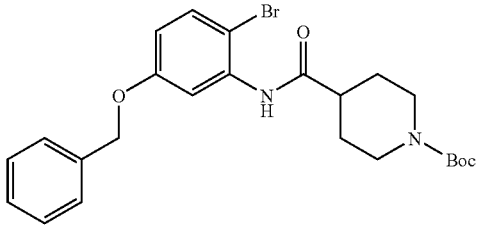

Piperidine-1,4-dicarboxylic acid mono-tert-butyl ester (2.25 g, 9.80 mmol) was dissolved in dry methylene chloride (18 mL) and dry pyridine (2.02 mL). To the reaction mixture was then added thionyl chloride (1.40 g, 11.76 mmol) under nitrogen atmosphere and the reaction mixture was stirred at room temperature for 30 minutes. To the reaction mixture was then added successively, under nitrogen atmosphere, 5-benzyloxy-2-bromo-phenylamine (3.0 g, 10.78 mmol), dry triethylamine (3.50 g, 34.32 mmol), dry methylene chloride (20 mL), 4-(dimethylamino)pyridine (0.12 g, 0.98 mmol) and the reaction mixture was stirred at room temperature for 24 hours. The reaction mixture was then partitioned with aqueous 2N HCl and tert-butyl methyl ether. The organic layer was washed with aqueous 2N HCl, aqueous NaHCO$_3$, brine, dried with Na$_2$SO$_4$, filtered and the solvent evaporated in vacuo to yield a crude oil. The crude oil was recrystallized from ethyl acetate/hexanes to yield the title compound as a solid.

$^1$H NMR (300 MHz, CDCl$_3$) δ7.66 (1H, bs), 7.50-7.32 (5H, m), 7.21 (1H, bs), 6.75-6.71 (1H, m), 5.15 (2H, s), 4.20 (2H, bs), 2.82-2.71 (2H, m), 2.37-2.32 (1H, m), 1.87-1.80 (2H, m), 1.78-1.70 (2H, m), 1.47 (9H, s) MS (ES$^+$) m/z 513.1 (M+H)$^+$

EXAMPLE 4

4-(2-Bromo-4-isopropyl-phenylcarbamoyl)-piperidine-1-carboxylic acid tert-butyl ester

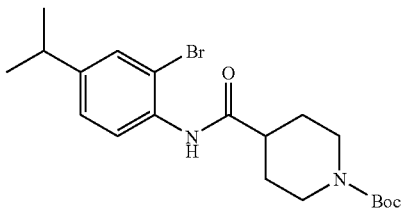

Piperidine-1,4-dicarboxylic acid mono-tert-butyl ester (2.97 g, 13 mmol) was dissolved in dry methylene chloride (25 mL) and dry pyridine (2.7 mL). To the reaction mixture was then added thionyl chloride (1.86 g, 15.6 mmol) under nitrogen atmosphere and the reaction mixture was stirred at room temperature for 30 minutes. To the reaction mixture was then added successively, under nitrogen atmosphere, 2-bromo-4-isopropyl-phenylamine (3.0 g, 14 mmol), dry triethylamine (4.6 g, 45.5 mmol), dry methylene chloride (20 mL), 4-(dimethylamino)pyridine (0.16 g, 1.3 mmol) and the reaction mixture was stirred at room temperature for 24 hours. The reaction mixture was then partitioned with aqueous 2N HCl and tert-Butyl methyl ether. The organic layer was washed with aqueous 2N HCl, aqueous NaHCO$_3$, brine, dried with Na$_2$SO$_4$, filtered and the solvent evaporated in vacuo to yield a crude oil. The crude oil was recrystallized from ethyl acetate/hexanes to yield the title compound as a solid.

$^1$H NMR (300 MHz, CDCl$_3$) δ 8.2. (1H, d), 7.6(1H, bs), 7.39 (1H, bs), 7.26 (1H, m), 4.2 (2H, bs), 2.85(3H, m), 2.4 (1H, m), 1.9 (2H, d), 1.75 (2H, m), 1.47 (9H, s), 1.2 (6H, m) MS (ES$^+$) m/z 447.1 (MNa.)

EXAMPLE 5

4-(2-Bromo-3-methyl-phenylcarbamoyl)-piperidine-1-carboxylic acid tert-butyl ester

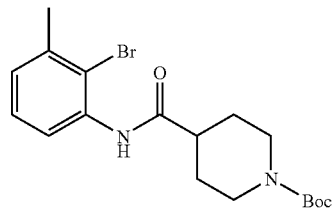

Piperidine-1,4-dicarboxylic acid mono-tert-butyl ester (5.0 g, 21.80 mmol) was dissolved in dry methylene chloride (32 mL) and dry pyridine (4.50 mL). To the reaction mixture was then added thionyl chloride (3.11 g, 26.17 mmol) under nitrogen atmosphere and the reaction mixture was stirred at room temperature for 30 minutes. To the reaction mixture was then added successively, under nitrogen atmosphere, 2-bromo-3-methyl-phenylamine (as described in *J. Org. Chem.* 1998, 53, 1170-1176) (4.46 g, 23.99 mmol), dry triethylamine (7.72 g, 76.33 mmol), dry methylene chloride (40 mL), 4-(dimethylamino)pyridine (0.26 g, 2.18 mmol) and the reaction mixture was stirred at room temperature for 24 hours. The reaction mixture was then partitioned with aqueous 2N HCl and tert-butyl methyl ether. The organic layer was washed with aqueous 2N HCl, aqueous NaHCO$_3$, brine, dried with Na$_2$SO$_4$, filtered and the solvent evaporated in vacuo to yield a crude oil. The crude oil was purified via flash chromatography (30% ethyl acetate/hexanes) to yield the title compound as a solid.

$^1$H NMR (300 MHz, CDCl$_3$) δ 8.16 (1H, d, J=8.2 Hz), 7.82 (1H, bs), 7.23-7.18 (1H, m), 7.02-6.99 (1H, m), 4.19-4.11 (2H, m), 2.86-2.78 (2H, m), 2.51-2.44 (1H, m), 2.42 (3H, s), 2.04-1.96 (2H, m), 1.78-1.69 (2H, m), 1.47 (9H, s) MS (ES$^+$) m/z 419.0 (M+H)$^+$

EXAMPLE 6

4-(2-Bromo-4-trifluoromethyl-phenylcarbamoyl)-piperidine-1-carboxylic acid tert-butyl ester

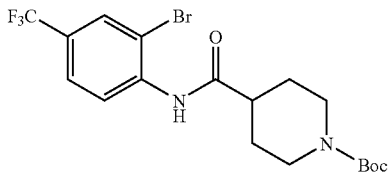

Piperidine-1,4-dicarboxylic acid mono-tert-butyl ester (4.90 g, 21.00 mmol) was dissolved in dry methylene chloride (30 mL) and dry pyridine (4.30 mL). To the reaction mixture was then added thionyl chloride (3.00 g, 25.20 mmol) under nitrogen atmosphere and the reaction mixture was stirred at room temperature for 30 minutes. To the reaction mixture was then added successively, under nitrogen atmosphere, 2-bromo-4-trifluoromethyl-phenylamine (5.60 g, 23.50 mmol), dry triethylamine (7.43 g, 73.5 mmol), dry methylene chloride (38 mL), 4-(dimethylamino)pyridine (0.26 g, 2.18 mmol) and the reaction mixture was stirred at room temperature for 24 hours. The reaction mixture was then partitioned with aqueous 2N HCl and tert-butyl methyl ether. The organic layer was washed with aqueous 2N HCl, aqueous NaHCO$_3$, brine, dried with Na$_2$SO$_4$, filtered and the solvent evaporated in vacuo to yield a crude oil. The crude oil was purified via flash chromatography (30% ethyl acetate/hexanes) to yield the title compound as an oil.

$^1$H NMR (300 MHz, CDCl$_3$) δ 8.5 (1H, d, J=9 Hz), 7.6 (1H, bs) 7.5 (1H, d, J=7.0 Hz), 7.3 (1H, d, J=8 Hz), 4.18 (2H, m), 2.8 (2H, m), 1.9 (2H, d), 1.8 (2H, m), 1.47 (9H, s) MS (ES$^+$) m/z 475.0 (MNa)$^+$

EXAMPLE 7

4-(2-Bromo-4-fluoro-phenylcarbamoyl)-piperidine-1-carboxylic acid tert-butyl ester

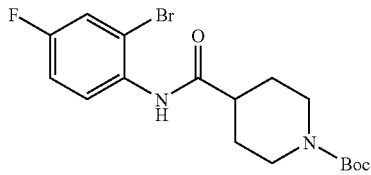

Piperidine-1,4-dicarboxylic acid mono-tert-butyl ester (16.5 g, 72.00 mmol) was dissolved in dry methylene chloride (100 mL) and dry pyridine (15 mL). To the reaction mixture was then added thionyl chloride (10.28 g, 86.40 mmol) under nitrogen atmosphere and the reaction mixture was stirred at room temperature for 30 minutes. To the reaction mixture was then added successively, under nitrogen atmosphere, 2-bromo-4-fluoro-phenylamine (15.0 g, 79.00 mmol), dry triethylamine (25.50 g, 252.0 mmol), dry methylene chloride (120 mL), 4-(dimethylamino)pyridine (0.87 g, 7.20 mmol) and the reaction mixture was stirred at room temperature for 24 hours. The reaction mixture was then partitioned with aqueous 2N HCl and tert-butyl methyl ether. The organic layer was washed with aqueous 2N HCl, aqueous NaHCO$_3$, brine, dried with Na$_2$SO$_4$, filtered and the solvent evaporated in vacuo to yield the title compound as a solid.

$^1$H NMR (300 MHz, CDCl$_3$) δ 8.3 (1H, m), 7.5 (1H, bs), 7.3 (1H, dd), 7.09 (1H, m), 4.19-4.15 (2H, m), 2.85-2.79 (3H, m), 1.98 (2H, m), 1.79-1.66 (2H, m), 1.47 (9H, s) MS (ES$^+$) m/z 425.0 (MNa)$^+$

EXAMPLE 8

4-[Benzyl-(2-bromo-phenyl)-carbamoyl]-piperidine-1-carboxylic acid tert-butyl ester

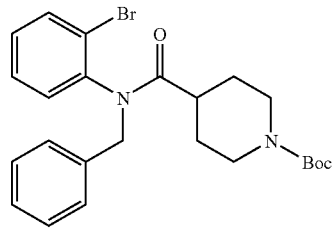

4-(2-Bromo-phenylcarbamoyl)-piperidine-1-carboxylic acid tert-butyl ester (0.50 g, 1.30 mmol) was dissolved in dry N,N-dimethylformamide (5.0 mL). To the reaction mixture was then added at 0° C. sodium hydride (60% in mineral oil, 63.6 mg, 1.59 mmol) under nitrogen atmosphere and the reaction mixture was stirred at 0° C. for one hour. To the reaction mixture was then added at 0° C. benzyl bromide (0.267 g, 1.56 mmol). The reaction mixture was stirred at 0° C. for one hour, then at room temperature under nitrogen atmosphere for 1 day. The reaction mixture was then added into an excess of water-ice and a gum formed. The gum was filtered by suction, washed with water and dried to yield a crude solid. The crude solid was purified via flash chromatography (30% ethyl acetate/hexanes) to yield the title compound as a solid.

$^1$H NMR (300 MHz, CDCl$_3$) δ7.74-7.67 (1H, m), 7.32-7.13 (7H, m), 6.78-6.73 (1H, m), 5.62 (1H, d, J=14.3 Hz), 4.15-4.04 (2H, m), 3.97 (1H, d, J=14.3 Hz), 2.50-2.26 (2H, m), 2.11-2.02 (1H, m), 1.92-1.45 (4H, m), 1.42 (9H, s)

MS (ES$^+$) m/z 497.2 (M+H)$^+$

EXAMPLE 9

4-[(2-Bromo-phenyl)-methyl-carbamoyl]-piperidine-1-carboxylic acid tert-butyl ester

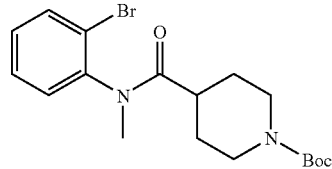

4-(2-Bromo-phenylcarbamoyl)-piperidine-1-carboxylic acid tert-butyl ester (0.50 g, 1.30 mmol) was dissolved in dry N,N-dimethylformamide (5.0 mL). To the reaction mixture was then added at 0° C. sodium hydride (60% in mineral oil, 62.6 mg, 1.56 mmol) under nitrogen atmosphere and the reaction mixture was stirred at 0° C. for one hour. To the reaction mixture was then added at 0° C. methyl iodide (0.241 g, 1.70 mmol). The reaction mixture was stirred at 0° C. for one hour, then at room temperature under nitrogen atmosphere for 3 hours. The reaction mixture was then added into an excess of water-ice and a gum formed. The gum was filtered by suction, washed with water and dried to yield a crude solid. The crude solid was purified via flash chromatography (25% ethyl acetate/hexanes) to yield the title compound as a solid.

$^1$H NMR (300 MHz, CDCl$_3$) δ 7.73-7.70 (1H, m), 7.43-7.38 (1H, m), 7.30-7.25 (2H, m), 4.28-4.04 (2H, m), 3.18 (3H, s), 2.55-2.38 (2H, m), 2.13-2.03 (1H, m), 1.85-1.45 (4H, m), 1.42 (9H, s)

MS (ES$^+$) m/z 419.0 (MNa)$^+$

EXAMPLE 10

4-{(2-Bromo-phenyl)-[2-(tetrahydro-pyran-2-yloxy)-ethyl]-carbamoyl}-piperidine-1-carboxylic acid tert-butyl ester

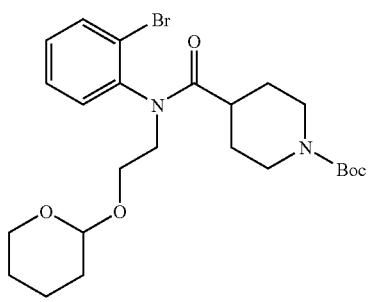

4-(2-Bromo-phenylcarbamoyl)-piperidine-1-carboxylic acid tert-butyl ester (1.0 g, 2.60 mmol) was dissolved in dry N,N-dimethylformamide (10.0 mL). To the reaction mixture was then added at 0° C. sodium hydride (60% in mineral oil, 127.3 mg, 3.18 mmol) under nitrogen atmosphere and the reaction mixture was stirred at 0° C. for one hour. To the reaction mixture was then added at 0° C., 2-(2-bromo-ethoxy)-tetrahydro-pyran (0.6 g, 2.86 mmol). The reaction mixture was stirred at 0° C. for one hour, then at room temperature under nitrogen atmosphere for 18 hours. The reaction mixture was then partitioned with water-ice and methylene chloride. The organic layer was washed with brine, dried with Na$_2$SO$_4$, filtered and the solvent evaporated in vacuo to yield a crude oil. The crude oil was purified via flash chromatography (25% ethyl acetate/hexanes) to yield the title compound as a gum.

$^1$H NMR (300 MHz, CDCl$_3$) δ 7.71-7.68 (1H, m), 7.42-7.35 (2H, m), 7.29-7.23 (1H, m), 4.61-4.22 (2H, m), 4.13-3.92 (3H, m), 3.82-3.69 (2H, m), 3.56-3.18 (2H, m), 2.55-2.37 (2H, m), 2.12-2.02 (1H, m), 1.85-1.45 (10H, m), 1.42 (9H, s)

MS (ES$^+$) m/z 534.2 (MNa)$^+$

EXAMPLE 11

4-[(2-Bromo-phenyl)-cyclohexylmethyl-carbamoyl]-piperidine-1-carboxylic acid tert-butyl ester

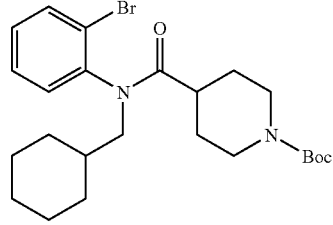

4-(2-Bromo-phenylcarbamoyl)-piperidine-1-carboxylic acid tert-butyl ester (1.0 g, 2.60 mmol) was dissolved in dry N,N-dimethylformamide (10.0 mL). To the reaction mixture was then added at 0° C. sodium hydride (60% in mineral oil, 127.3 mg, 3.18 mmol) under nitrogen atmosphere and the reaction mixture was stirred at 0° C. for one hour. To the reaction mixture was then added at 0° C., bromomethyl-cyclohexane (0.55 g, 3.13 mmol). The reaction mixture was stirred at 0° C. for one hour, then at room temperature under nitrogen atmosphere for 18 hours. The reaction mixture was then added into an excess of water-ice and a solid precipitated. The solid was filtered by suction, washed with water and dried to yield a crude solid. The crude solid was purified via flash chromatography (25% ethyl acetate/hexanes) to yield the title compound as a solid.

$^1$H NMR (300 MHz, CDCl$_3$) δ7.74-7.70 (1H, m), 7.43-7.37 (1H, m), 7.30-7.22 (2H, m), 4.10-4.0 (3H, m), 2.91-2.84 (1H, m), 2.55-2.30 (2H, m), 2.04-1.98 (1H, m), 1.82-1.44 (9H, m), 1.42 (9H, s), 1.2-0.96 (6H, m)

MS (ES$^+$) m/z 503.2 (MNa)$^+$

EXAMPLE 12

4-[(2-Bromo-5-methoxy-phenyl)-ethyl-carbamoyl]-piperidine-1-carboxylic acid tert-butyl ester

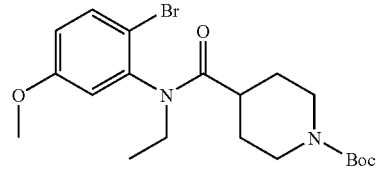

4-(2-Bromo-5-methoxy-phenylcarbamoyl)-piperidine-1-carboxylic acid tert-butyl ester (0.5 g, 1.21 mmol) was dissolved in dry N,N-dimethylformamide (5.0 mL). To the reaction mixture was then added at 0° C. sodium hydride (60% in mineral oil, 60.0 mg, 1.45 mmol) under nitrogen atmosphere and the reaction mixture was stirred at 0° C. for one hour. To the reaction mixture was then added at 0° C., ethyl iodide (0.226 g, 1.45 mmol). The reaction mixture was stirred at 0° C. for one hour, then at room temperature under nitrogen atmosphere for 18 hours. The reaction mixture was then added into an excess of water-ice and a solid precipitated. The solid was filtered by suction, washed with water and dried to yield a crude solid. The crude solid was purified via flash chromatography (25% ethyl acetate/hexanes) to yield the title compound as a solid.

$^1$H NMR (300 MHz, CDCl$_3$) δ 7.59 (1H, d, J=8.8 Hz), 6.86-6.82 (1H, m), 6.76 (1H, d, J=2.95 Hz), 4.07-3.98 (3H, m), 3.82 (3H, s), 3.39-3.32 (1H, m), 2.50-2.30 (2H, m), 2.09-2.04 (1H, m), 1.81-1.46 (4H, m), 1.42 (9H, s)

MS (ES$^+$) m/z 465.1 (MNa)$^+$

EXAMPLE 13

4-[(2-Bromo-5-methoxy-phenyl)-cyclopropylmethyl-carbamoyl]-piperidine-1-carboxylic acid tert-butyl ester

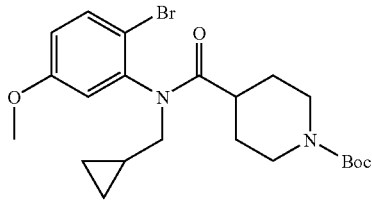

The title compound was prepared according to the process outlined in Example 12 above, to yield a solid.

$^1$H NMR (300 MHz, CDCl$_3$) δ 7.57 (1H, d, J=8.8 Hz), 6.88-6.82 (2H, m), 4.07-3.98 (2H, m), 3.94-3.87 (1H, m), 3.82 (3H, s), 3.16-3.09 (1H, m), 2.50-2.30 (2H, m), 2.11-2.08 (1H, m), 1.82-1.45 (4H, m), 1.42 (9H, s), 0.97-0.92 (1H, m), 0.45-0.39 (2H, m), 0.12-0.06 (2H, m)

MS (ES$^+$) m/z 491.0 (MNa)$^+$.

EXAMPLE 14

4-[(2-Bromo-4-isopropyl-phenyl)-propyl-carbamoyl]-piperidine-1-carboxylic acid tert-butyl ester

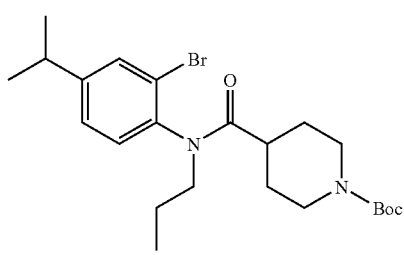

The title compound was prepared according to the process outlined in Example 12 above, to yield an oil.

$^1$H NMR (300 MHz, CDCl$_3$) δ7.55 (1H, d, J=1.90 Hz), 7.23-7.20 (1H, m), 7.11 (1H, d, J=8.02 Hz), 4.03-3.93 (3H, m), 3.16-3.09 (1H, m), 3.06-2.92 (1H, m), 2.50-2.30 (2H, m), 2.08-2.01 (1H, m), 1.81-1.44 (6H, m), 1.42 (9H, s), 1.28 (6H, d, J=6.92 Hz), 0.90-0.85 (3H, m)

MS (ES$^+$) m/z 491.2 (MNa)$^+$.

EXAMPLE 15

4-[(2-Bromo-3-methyl-phenyl)-methyl-carbamoyl]-piperidine-1-carboxylic acid tert-butyl ester

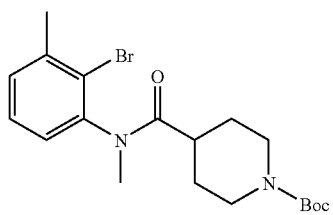

The title compound was prepared according to the process outlined in Example 12 above, to yield a foam.

$^1$H NMR (300 MHz, CDCl$_3$) δ 7.29-7.27 (1H, m), 7.11-7.08 (2H, m), 4.03-3.93 (2H, m), 3.17 (3H, s), 2.49 (3H, s), 2.49-2.30 (2H, m), 2.10-2.04 (1H, m), 1.82-1.45 (4H, m), 1.42 (9H, s)

MS (ES$^+$) m/z 435.1 (MNa)$^+$

EXAMPLE 16

4-[(2-Bromo-4-trifluoromethyl-phenyl)-methyl-carbamoyl]-Piperidine-1-carboxylic acid tert-butyl ester

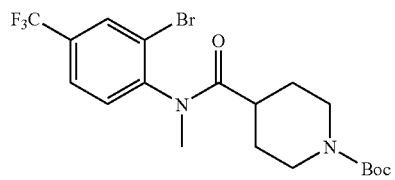

The title compound was prepared according to the process outlined in Example 12 above, to yield an oil.

$^1$H NMR (300 MHz, CDCl$_3$) δ 8.01 (1H, m), 7.7 (2H, d), 7.4 (1H, d) 4.04 (2H, m), 3.19 (3H, s), 2.49 (3H, m), 2.15 (2H, m), 1.7-1.65 (2H, m), 1.43 (9H, s)

MS (ES$^+$) m/z 489.0 (MNa)$^+$.

EXAMPLE 17

4-[(2-Bromo-4-fluoro-phenyl)-methyl-carbamoyl]-piperidine-1-carboxylic acid tert-butyl ester

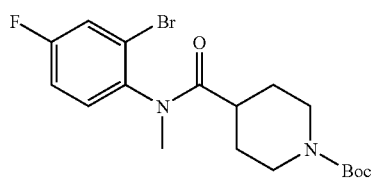

The title compound was prepared according to the process outlined in Example 12 above, to yield a solid.

$^1$H NMR (300 MHz, CDCl$_3$) δ 7.47 (1H, d), 7.29 (1H, m), 7.15 (1H, m) 4.04 (2H, m), 3.16 (3H, s), 2.49 (2H, m), 2.05 (1H, m), 1.82-1.65 (4H, m), 1.43 (9H, s)

MS (ES$^+$) m/z 437.0 (MNa)$^+$.

EXAMPLE 18

4-[(2-Bromo-4-isopropyl-phenyl)-methyl-carbamoyl]-piperidine-1-carboxylic acid tert-butyl ester

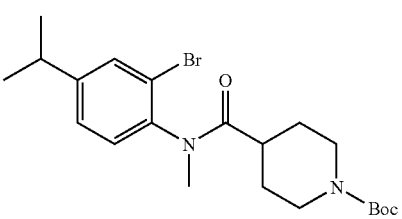

The title compound was prepared according to the process outlined in Example 12 above, to yield an oil.

$^1$H NMR (300 MHz, CDCl$_3$) δ7.54 (1H, m), 7.28-7.18 (2H, m), 4.03 (2H, m), 3.16 (3H, s), 2.97-2.94 (1H, m), 2.49-2.30 (2H, m), 2.13 (1H, m), 1.83-1.45 (4H, m), 1.42 (9H, s), 1.29-1.27 (6H, d)

MS (ES$^+$) m/z 461.0 (MNa)$^+$.

EXAMPLE 19

4-[(2-Bromo-phenyl)-methoxycarbonylmethyl-carbamoyl]-piperidine-1-carboxylic acid tert-butyl ester

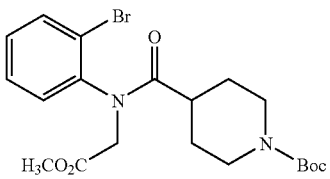

The title compound was prepared according to the process outlined in Example 12 above, to yield an oil.

$^1$H NMR (300 MHz, CDCl$_3$) δ 7.72-7.63 (2H, m), 7.41-7.38 (1H, m), 7.30-7.24 (1H, m), 4.98 (1H, d), 4.09-3.92 (2H, m), 3.72 (3H, s), 3.58 (1H, d), 2.55-2.38 (2H, m), 2.20-2.11 (1H, m), 1.78-1.56 (4H, m), 1.42 (9H, s)

MS (ES$^+$) m/z 477.1 (MNa)$^+$.

EXAMPLE 20

1-(Methoxycarbonyl-methyl)-spiro[indoline-3,4'-piperidin]-2-one

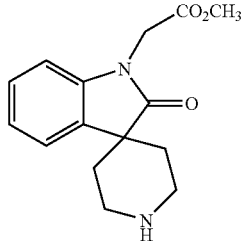

The title compound was prepared according to the procedure described in *Org. Prep. Proced. Int.* (1995), 27(6), 691-694 to yield a solid.

$^1$H NMR (300 MHz, CDCl$_3$) δ 7.46-7.41 (1H, m), 7.29-7.25 (1H, m), 7.11-7.06 (1H, m), 6.74-6.71 (1H, m), 4.47 (2H, s), 3.75 (3H, s), 3.44-3.36 (2H, m), 3.12-3.05 (2H, m), 2.11 (1H, bs), 1.94-1.76 (4H, m)

MS (ES$^+$) m/z 275.0 (M+H)$^+$

EXAMPLE 21

1-((tetrahydropyran-2-yl)oxy-ethyl)-5-tert-butoxy-carbonyl-spiro[indoline-3,4'-piperidin]-2-one (Compound #47)

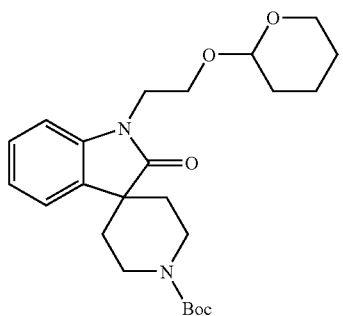

Pd(dba)$_2$ (0.068 g, 0.109 mmol), rac-BINAP (0.078 g, 0.085 ml) and sodium tert-butoxide (0.22 g, 2.28 mmol) were combined into a pressure flask. To the reaction mixture was then added dry 1,4-dioxane (3 mL) under nitrogen and the resulting mixture stirred for 1 minute. To the reaction mixture was then added, under nitrogen, a solution of 4-{(2-bromo-phenyl)-[2-(tetrahydro-pyran-2-yloxy)-ethyl]-carbamoyl}-piperidine-1-carboxylic acid tert-butyl ester (0.78 g, 1.52 mmol) in dry 1,4-dioxane (9 mL). The pressure flask was sealed and degassed under high vacuum and left under nitrogen. The reaction mixture was stirred at 110° C. for 6 hours and then partitioned with aqueous 0.5 M citric acid, water and methylene chloride. The organic layer was washed with brine, dried with Na$_2$SO$_4$, filtered and the solvent evaporated in vacuo to yield a solid. The solid was purified via flash chromatography (50% ethyl acetate/hexanes) to yield the title compound as a foam.

$^1$H NMR (300 MHz, CDCl$_3$) δ 7.28-7.24 (2H, m), 7.06-7.01 (2H, m), 4.61-4.59 (1H, m), 3.99-3.62 (9H, m), 3.46-3.41 (1H, m), 1.85-1.39 (19H, m)

MS (ES$^+$) m/z 453.3 (MNa)$^+$

EXAMPLE 22

1-(4-methoxy-benzyl)-5-tert-butoxy-carbonyl-spiro[indoline-3,4'-piperidin]-2-one (Compound #48)

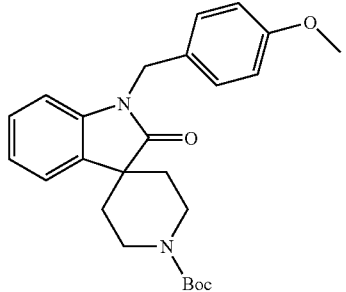

The title compound was prepared according to the procedure outlined in Example 21 above, to yield a foam.

$^1$H NMR (300 MHz, CDCl$_3$) δ 7.29-7.26 (2H, m), 7.25-7.15 (3H, m), 7.04-6.99 (1H, m), 6.86-6.82 (2H, m), 6.77-6.75 (1H, m), 4.84 (2H, s), 3.93-3.82 (4H, m), 3.77 (3H, s), 1.90-1.79 (4H, m), 1.51 (9H, s)

MS (ES$^+$) m/z 445.1 (MNa)$^+$.

EXAMPLE 23

1-(cyclohexyl-methyl)-5-tert-butoxycarbonyl-spiro[indoline-3,4'-piperidin]-2-one (Compound #51)

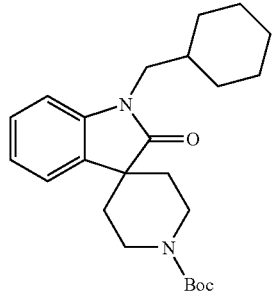

The title compound was prepared according to the procedure outlined in Example 21 above, to yield a foam.

$^1$H NMR (300 MHz, CDCl$_3$) δ 7.30-7.24 (2H, m), 7.07-7.02 (1H, m), 6.86 (1H, d, J=7.7 Hz), 3.91-3.79 (4H, m), 3.52 (2H, d, J=7.4 Hz), 1.85-1.62 (5H, m), 1.50 (9H, s), 1.47-1.01 (10H, m)

MS (ES$^+$) m/z 421.0 (Mna)$^+$

EXAMPLE 24

1-ethyl-5-tert-butoxycarbonyl-10-methoxy-spiro[indoline-3,4'-piperidin]-2-one (Compound #38)

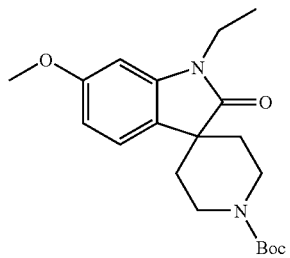

The title compound was prepared according to the procedure outlined in Example 21 above, to yield an oil.

$^1$H NMR (300 MHz, CDCl$_3$) δ 7.20 (1H, d, J=8.2 Hz), 6.54 (1H, dd, J=2.3 and 8.2 Hz), 6.46 (1H, d, J=2.3 Hz), 3.91-3.83 (5H, m), 3.81-3.68 (4H, m), 1.86-1.65 (4H, m), 1.50 (9H, s), 1.28-1.22 (3H, m)

MS (ES$^+$) m/z 383.2 (MNa)$^+$

EXAMPLE 25

1-(cyclopropyl-methyl)-5-tert-butoxycarbonyl-10-methoxy-spiro[indoline-3,4'-piperidin]-2-one (Compound #54)

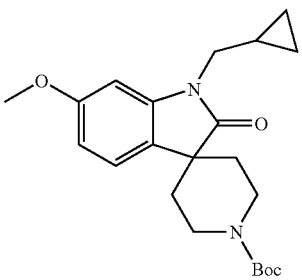

The title compound was prepared according to the procedure outlined in Example 21 above, to yield a foam.

$^1$H NMR (300 MHz, CDCl$_3$) δ 7.20 (1H, d, J=8.0 Hz), 6.57-6.52 (2H, m), 3.91-3.81 (5H, m), 3.74-3.69 (2H, m), 3.56 (2H, d, J=6.8 Hz), 1.87-1.70 (4H, m), 1.50 (9H, s), 1.17-1.13 (1H, m), 0.54-0.48 (2H, m), 0.39-0.34 (2H, m)

MS (ES$^+$) m/z 409.1 (MNa)$^+$.

EXAMPLE 26

1-methyl-5-tert-butoxycarbonyl-10-methoxy-spiro[indoline-3,4'-piperidin]-2-one (Compound #34)

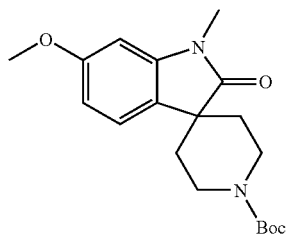

The title compound was prepared according to the procedure outlined in Example 21 above, to yield an oil.

$^1$H NMR (300 MHz, CDCl$_3$) δ 7.20 (1H, d, J=8.2 Hz), 6.55 (1H, dd, J=2.3 and 8.2 Hz), 6.44 (1H, d, J=2.3 Hz), 3.92-3.83 (5H, m), 3.73-3.68 (2H, m), 3.18 (3H, s), 1.87-1.69 (4H, m), 1.50 (9H, s)

MS (ES$^+$) m/z 369.1 (MNa)$^+$.

EXAMPLE 27

1-ethyl-5-tert-butoxycarbonyl-9-isopropyl-spiro[indoline-3,4'-piperidin]-2-one (Compound #33)

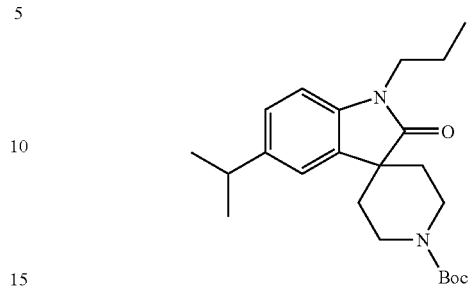

The title compound was prepared according to the procedure outlined in Example 21 above, to yield an oil.

$^1$H NMR (300 MHz, CDCl$_3$) δ 7.14-7.11 (2H, m), 6.79 (1H, d, J=7.9 Hz), 3.86-3.82 (4H, m), 3.67-3.62 (2H, m), 2.92-2.87 (1H, m), 1.84-1.65 (6H, m), 1.51 (9H, s), 1.25 (6H, d, J=6.9 Hz), 0.96-0.91 (3H, m)

MS (ES$^+$) m/z 409.1 (MNa)$^+$.

EXAMPLE 28

1-methyl-5-tert-butoxycarbonyl-9-methyl-spiro[indoline-3,4'-piperidin]-2-one (Compound #56)

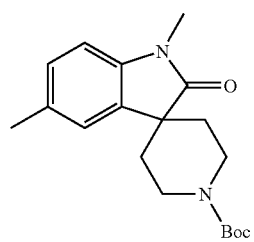

The title compound was prepared according to the procedure outlined in Example 21 above, to yield a solid.

$^1$H NMR (300 MHz, CDCl$_3$) δ7.10-7.08 (2H, m), 6.76-6.73 (1H, m), 3.89-3.78 (4H, m), 3.18 (3H, s), 2.35 (3H, s), 1.85-1.73 (4H, m), 1.50 (9H, s)

MS (ES$^+$) m/z 353.0 (MNa)$^+$.

EXAMPLE 29

1-methyl-5-tert-butoxycarbonyl-9-isopropyl-spiro[indoline-3,4'-piperidin]-2-one (Compound #6)

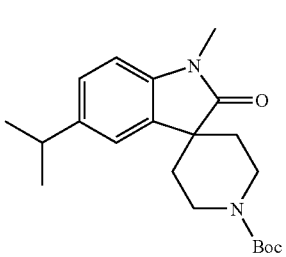

The title compound was prepared according to the procedure outlined in Example 21 above, to yield an oil.

$^1$H NMR (300 MHz, CDCl$_3$) δ7.17-7.14 (2H, m), 6.79-6.76 (1H, m), 3.86-3.82 (4H, m), 3.18 (3H, s), 2.92-2.88 (1H, m), 1.85-1.76 (4H, m), 1.51 (9H, s), 1.25 (6H, d, J=6.9 Hz)

MS (ES$^+$) m/z 381.0 (MNa)$^+$.

EXAMPLE 30

1-methyl-5-tert-butoxycarbonyl-9-fluoro-spiro[indoline-3,4'-piperidin]-2-one (Compound #10)

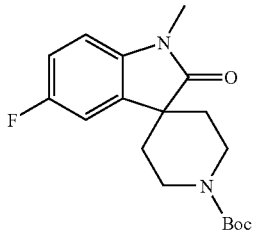

The title compound was prepared according to the procedure outlined in Example 21 above, to yield a solid.

$^1$H NMR (300 MHz, CDCl$_3$) δ 7.05-6.96 (2H, m), 6.79-6.75 (1H, m), 3.89-3.78 (4H, m), 3.19 (3H, s), 1.85-1.71 (4H, m), 1.50 (9H, s)

MS (ES$^+$) m/z 357.1 (MNa)$^+$.

EXAMPLE 31

1-methyl-5-tert-butoxycarbonyl-9-trifluoromethyl-spiro[indoline-3,4'-piperidin]-2-one (Compound #14)

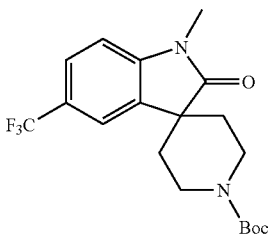

The title compound was prepared according to the procedure outlined in Example 21 above, to yield an oil.

$^1$H NMR (300 MHz, CDCl$_3$) δ 7.60-7.56 (2H, m), 7.48 (1H, s) 6.92-6.89 (1H, m), 3.89-3.78 (4H, m), 3.20 (3H, s), 1.85-1.76 (4H, m), 1.50 (9H, s)

MS (ES$^+$) m/z 407.0 (MNa)$^+$.

EXAMPLE 32

1-(methylcarbonyloxy-ethyl)-5-tert-butoxycarbonyl-spiro[indoline-3,4'-piperidin]-2-one (Compound #53)

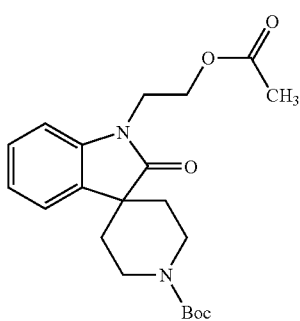

1-(tetrahydropyran-2-yl-oxy-ethyl)-5-tert-butoxycarbonyl-spiro[indoline-3,4'-piperidin]-2-one (0.021 g, 0.05 mmol) was dissolved in methanol (2 mL). To the reaction mixture was then added at room temperature aqueous 1.0N HCl (80 μL) and the reaction mixture was stirred for 30 minutes. The reaction mixture was then partitioned with aqueous Na$_2$CO$_3$ and ethyl acetate. The organic layer was washed with brine, dried with Na$_2$SO$_4$, filtered and the solvent evaporated in vacuo to yield a solid. The solid was then dissolved in dry dichloromethane (2 mL). To the reaction mixture was then added at 0° C. triethylamine (0.12 g, 0.12 mmol) and acetic anhydride (0.02 g, 0.2 mmol) under nitrogen atmosphere and the reaction mixture was stirred at 0° C. for 30 minutes and 18 hrs at room temperature. The reaction mixture was then partitioned with aqueous Na$_2$CO$_3$ and dichloromethane. The organic layer was washed with brine, dried with Na$_2$SO$_4$, filtered and the solvent evaporated in vacuo to yield the title compound as a gum.

$^1$H NMR (300 MHz, CDCl$_3$) δ 7.30-7.25 (2H, m), 7.09-7.04 (1H, m), 6.94-6.91 (1H, m), 4.34-4.30 (2H, m), 3.98-3.94 (2H, m), 3.90-3.80 (4H, m), 1.96 (3H, s), 1.85-1.79 (4H, m), 1.50 (9H, s)

MS (ES$^+$) m/z 411.1 (MNa)$^+$

EXAMPLE 33

1-methyl-5-tert-butoxycarbonyl-spiro[indoline-3,4'-piperidin]-2-one (Compound #50)

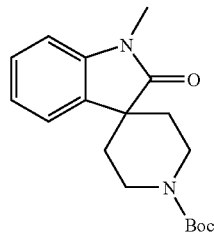

The title compound was prepared according to the procedure outlined in Example 21 above, to yield a gum.

$^1$H NMR (300 MHz, CDCl$_3$) δ 7.32-7.26 (2H, m), 7.09-7.04 (1H, m), 6.87-6.84 (1H, m), 3.91-3.70 (4H, m), 3.21 (3H, s), 1.86-1.70 (4H, m), 1.50 (9H, s)

MS (ES$^+$) m/z 339.1 (MNa)$^+$.

EXAMPLE 34

1-benzyl-5-tert-butoxycarbonyl-spiro[indoline-3,4'-piperidin]-2-one (Compound #49)

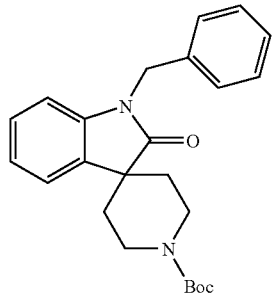

The title compound was prepared according to the procedure outlined in Example 21 above, to yield an oil.

$^1$H NMR (300 MHz, CDCl$_3$) δ7.34-7.24 (6H, m), 7.19-7.14 (1H, m), 7.05-7.00 (1H, m), 6.74 (1H, d, J=7.6 Hz), 4.90 (2H, s), 3.93-3.72 (4H, m), 1.92-1.71 (4H, m), 1.51 (9H, s)

MS (ES$^+$) m/z 415.1 (MNa)$^+$.

EXAMPLE 35

1-ethyl-10-methoxy-spiro[indoline-3,4'-piperidin]-2-one

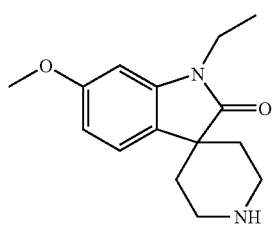

1-ethyl-10-methoxy-5-tert-butoxycarbonyl-spiro[indoline-3,4'-piperidin]-2-one (0.18 g, 0.5 mmol) was dissolved in dry dichloromethane (15 mL). To the reaction mixture was then added at 0° C. a solution of 30% trifluoroacetic acid in dichloromethane (5 mL) under nitrogen atmosphere and the reaction mixture was stirred at 0° C. for 30 minutes. The solvent was evaporated in vacuo to yield a crude oil. The crude oil was dissolved in dichloromethane (15 mL). To the reaction mixture was then added MP-Carbonate (from Argonaut, capacity ~3 mmol/g) (0.5 g) and the reaction mixture was stirred at room temperature for 2 hrs. The reaction mixture was then filtered, the resin washed with dichloromethane and the solvent evaporated in vacuo to yield a title compound as a foam.

$^1$H NMR (300 MHz, CDCl$_3$) δ 7.23 (1H, d, J=8.2 Hz), 6.60 (1H, dd, J=2.2 and 8.2 Hz), 6.45 (1H, d, J=2.2 Hz), 3.96-3.87 (2H, m), 3.83 (3H, s), 3.75-3.68 (2H, m), 3.39-3.34 (2H, m), 2.44-2.34 (2H, m), 1.87-1.78 (3H, m), 1.28-1.23 (3H, m)

MS (ES$^+$) m/z 261.1 (M+H)$^+$

EXAMPLE 36

1-(methylcarbonyloxy-ethyl)-spiro[indoline-3,4'-piperidin]-2-one

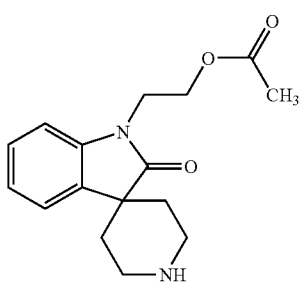

The title compound was prepared according to the procedure outlined in Example 35 above, to yield an oil.

$^1$H NMR (300 MHz, CDCl$_3$) δ7.42-7.39 (1H, m), 7.30-7.25 (1H, m), 7.10-7.05 (1H, m), 6.93-6.91 (1H, m), 4.34-4.30 (2H, m), 3.98-3.94 (2H, m), 3.52-3.44 (2H, m), 3.17-3.09 (2H, m), 2.45 (3H, bs), 1.96 (3H, s), 1.91-1.81 (2H, m)

MS (ES$^+$) m/z 289.0 (M+H)$^+$.

EXAMPLE 37

1-(4-methoxy-benzyl)-spiro[indoline-3,4'-piperidin]-2-one

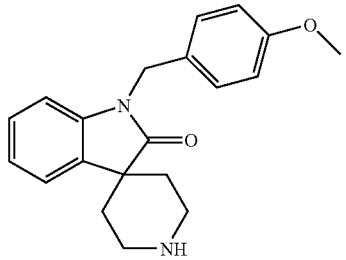

The title compound was prepared according to the procedure outlined in Example 35 above, to yield a foam.

$^1$H NMR (300 MHz, CDCl$_3$) δ7.38-7.36 (1H, m), 7.21-7.18 (3H, m), 7.17-7.06 (1H, m), 6.86-6.82 (2H, m), 6.78-6.76 (1H, m), 5.29 (1H, bs), 4.83 (2H, s), 3.79-3.71 (5H, m), 3.32-3.26 (2H, m), 2.26-2.16 (2H, m), 1.93-1.88 (2H, m)

MS (ES$^+$) m/z 323.2 (M+H)$^+$.

EXAMPLE 38

1-(cyclopropyl-methyl)-10-methoxy-spiro[indoline-3,4'-piperidin]-2-one

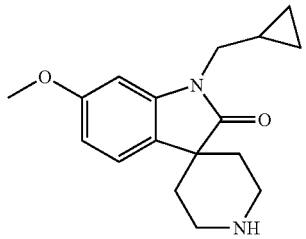

The title compound was prepared according to the procedure outlined in Example 35 above, to yield an oil.

$^1$H NMR (300 MHz, CDCl$_3$) δ7.22 (1H, d, J=8.2 Hz), 6.61 (1H, dd, J=2.2 and 8.2 Hz), 6.52 (1H, d, J=2.2 Hz), 4.73 (1H, bs), 3.95-3.86 (3H, m), 3.83 (3H, s), 3.55 (2H, d, J=6.9 Hz), 3.41-3.38 (2H, m), 2.41-2.33 (2H, m), 1.89-1.86 (2H, m), 0.55-0.50 (2H, m), 0.38-0.34 (2H, m)

MS (ES$^+$) m/z 287.1 (M+H)$^+$.

EXAMPLE 39

1-methyl-10-methoxy-spiro[indoline-3,4'-piperidin]-2-one

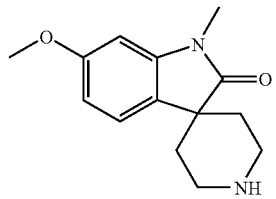

The title compound was prepared according to the procedure outlined in Example 35 above, to yield an oil.

$^1$H NMR (300 MHz, CDCl$_3$) δ 7.33 (1H, d, J=8.2 Hz), 6.56 (1H, dd, J=2.2 and 8.2 Hz), 6.44 (1H, d, J=2.2 Hz), 3.83 (3H, s), 3.40-3.32 (2H, m), 3.18 (3H, s), 3.11-3.02 (2H, m), 1.89-1.81 (3H, m), 1.71-1.67 (2H, m)

MS (ES$^+$) m/z 247.1 (M+H)$^+$.

EXAMPLE 40

1-ethyl-9-isopropyl-spiro[indoline-3,4'-piperidin]-2-one

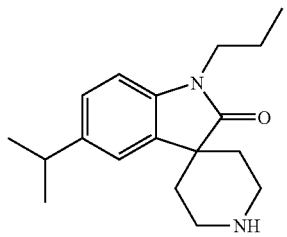

The title compound was prepared according to the procedure outlined in Example 35 above, to yield a foam.

$^1$H NMR (300 MHz, CDCl$_3$) δ7.20 (1H, bs), 7.16-7.13 (2H, m), 6.79 (1H, d, J=8.0 Hz), 3.94-3.85 (2H, m), 3.66-3.62 (2H, m), 3.38-3.34 (2H, m), 2.95-2.86 (1H, m), 2.43-2.32 (2H, m), 1.88-1.83 (2H, m), 1.76-1.64 (2H, m), 1.25 (6H, d, J=6.9 Hz), 0.97-0.92 (3H, m)

MS (ES$^+$) m/z 287.2 (M+H)$^+$.

EXAMPLE 41

1-methyl-9-methyl-spiro[indoline-3,4'-piperidin]-2-one

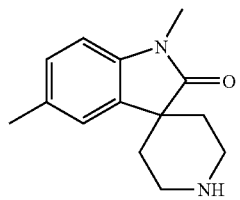

The title compound was prepared according to the procedure outlined in Example 35 above, to yield a foam.

$^1$H NMR (300 MHz, CDCl$_3$) δ7.13-7.10 (2H, m), 6.76-6.74 (1H, m), 3.96-3.89 (2H, m), 3.41-3.37 (2H, m), 3.18 (3H, s), 2.46-2.35 (5H, m), 1.89-1.84 (2H, m)

MS (ES$^+$) m/z 231.1 (M+H)$^+$.

EXAMPLE 42

1-(methylcarbonyloxy-methyl)-5-(cyclooctyl-methyl)-spiro[indoline-3,4'-piperidin]-2-one (Compound #1)

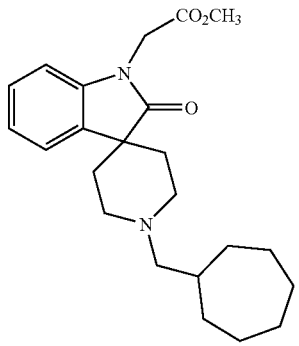

1-Bromomethyl-cyclooctane (0.026 g, 0.216 mmol) and 1-(methylcarbonyloxy-ethyl)-spiro[indoline-3,4'-piperidin]-2-one (0.029 g, 0.105 mmol) were dissolved in acetonitrile (1.5 mL). Potassium carbonate (0.044 g, 0.316 mmol) and a catalytic amount of potassium iodide were added and the reaction mixture was stirred at 45° C. under nitrogen atmosphere for 18 hours. The reaction mixture was then partitioned with water and ethyl acetate. The organic layer was washed with brine, dried with Na$_2$SO$_4$, filtered and the solvent evaporated in vacuo to yield a crude oil. The crude oil was purified via flash chromatography (3% methanol/dichloromethane) to yield the title compound as an oil.

$^1$H NMR (300 MHz, CDCl$_3$) δ 7.46 (1H, d, J=7.0 Hz), 7.27-7.22 (1H, m), 7.09-7.04 (1H, m), 6.72 (1H, d, J=7.7 Hz), 4.46 (2H, s), 3.76 (3H, s), 2.05-1.89 (4H, m), 1.72-1.62 (2H, m), 1.61-1.33 (12H, m), 1.28-1.23 (3H, m), 0.88-0.79 (2H, m)

MS (ES$^+$) m/z 385.2 (M+H)$^+$.

EXAMPLE 43

1-(methylcarbonyloxy-methyl)-5-(4-chlorobenzyl)-spiro[indoline-3,4'-piperidin]-2-one (Compound #39)

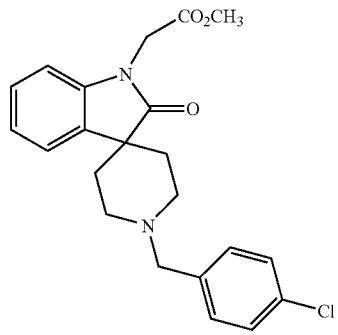

1-(Methylcarbonyloxy-methyl)-spiro[indoline-3,4'-piperidin]-2-one (0.026 g, 0.095 mmol) and 4-chloro-benzaldehyde (0.02 g, 0.14 mmol) were dissolved in dry 1,2-dichloroethane (1.5 mL). To the reaction mixture was then added glacial acetic acid (0.006 g, 0.095 mmol) under nitrogen atmosphere and the reaction mixture was stirred at room temperature for 30 minutes. To the reaction mixture was then added, at room temperature, sodium triacetoxyborohydride (0.034 g, 0.16 mmol) under nitrogen atmosphere and the reaction mixture was stirred at room temperature for 18 hours. The reaction mixture was then partitioned with aqueous NaHCO$_3$ and dichloromethane. The organic layer was washed with brine, dried with Na$_2$SO$_4$, filtered and the solvent evaporated in vacuo to yield a crude oil. The crude oil was purified via flash chromatography (2.5% methanol/dichloromethane) to yield the title compound as a solid.

$^1$H NMR (300 MHz, CDCl$_3$) δ7.42-7.37 (1H, m), 7.35-7.23 (5H, m), 7.12-7.05 (1H, m), 6.73-6.68 (1H, m), 4.46 (2H, s), 3.74 (3H, s), 3.63 (2H.s), 2.94-2.87 (2H, m), 2.74-2.64 (2H, m), 2.04-1.86 (4H, m)

MS (ES$^+$) m/z 399.1(M+H)$^+$

EXAMPLE 44

1-benzyl-5-(cyclooctyl-methyl)-spiro[indoline-3,4'-piperidin]-2-one (Compound #44)

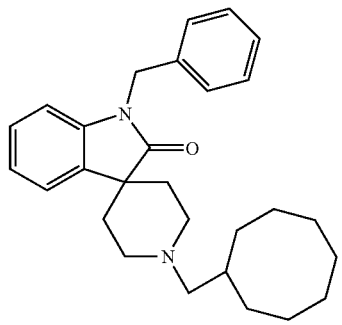

1-Bromomethyl-cyclooctane (0.087 g, 0.424 mmol) and 1-benzyl-spiro[indoline-3,4'-piperidin]-2-one (0.030 g, 0.141 mmol) were dissolved in dry N,N-dimethylformamide (3 mL). Potassium carbonate (0.078 g, 0.565 mmol) and a catalytic amount of potassium iodide were added. The reaction mixture was then stirred at 55° C. under nitrogen atmosphere for 18 hours. The reaction mixture was partitioned with water and ethyl acetate. The organic layer was washed with brine, dried with $Na_2SO_4$, filtered and the solvent evaporated in vacuo to yield a crude oil. The crude oil was purified via flash chromatography (50% ethyl acetate/hexanes) to yield the title compound as an oil.

$^1$H NMR (300 MHz, CDCl$_3$) δ 7.46 (1H, d, J=6.8 Hz), 7.33-7.24 (5H, m), 7.22-7.12 (1H, m), 7.03-6.91 (1H, m), 6.72 (1H, d, J=7.7 Hz), 4.90 (2H, s), 2.94-2.87 (2H, m), 2.69-2.61 (2H, m), 2.26 (1H, d, J=7.1 Hz), 2.08-2.00 (2H, m), 1.87-1.49 (15H, m), 1.31-1.24 (2H, m)

MS (ES$^+$) m/z 417.3 (M+H)$^+$

EXAMPLE 45

5-(cyclooctyl-methyl)-spiro[indoline-3,4'-piperidin]-2-one (Compound #18)

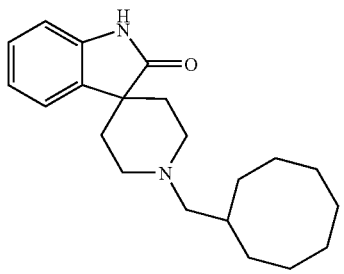

To a magnetically stirred solution of liquid ammonia (10 mL) was added lithium (20 mg) at −78° C. under nitrogen atmosphere causing the solution to turn dark-blue. To the reaction mixture was then added a solution of 1-benzyl-5-(cyclooctyl-methyl)-spiro[indoline-3,4'-piperidin]-2-one (0.025 g, 0.06 mmol) in dry THF (2 mL). The reaction mixture was stirred −78° C. under nitrogen atmosphere for a few minutes, then ammonium chloride was added and the reaction mixture was stirred at room temperature for one hour. The reaction mixture was partitioned with water and ethyl acetate. The organic layer was washed with brine, dried with $Na_2SO_4$, filtered and the solvent evaporated in vacuo to yield the title compound as a foam.

$^1$H NMR (300 MHz, CDCl$_3$) δ 7.96 (1H, bs), 7.45 (1H, d, J=7.5 Hz), 7.23-7.18 (1H, m), 7.04-6.99 (1H, m), 6.89 (1H, d, J=7.7 Hz), 3.85-3.80 (2H, m), 2.90-2.82 (2H, m), 2.66-2.56 (2H, m), 2.25 (1H, d, J=7.1 Hz), 2.05-1.97 (2H, m), 1.91-1.20 (17H, m)

MS (ES$^+$) m/z 327.2 (M+H)$^+$

EXAMPLE 46

1-methyl-5-(cyclooctyl-methyl)-spiro[indoline-3,4'-piperidin]-2-one (Compound #45)

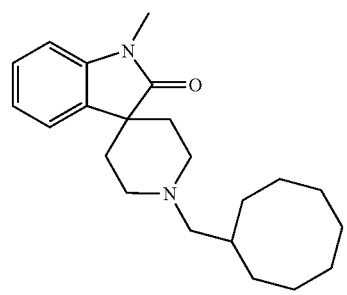

The title compound was prepared according to the procedure outlined in Example 42 above, to yield a solid.

$^1$H NMR (300 MHz, CDCl$_3$) δ 7.46 (1H, d, J=7.1 Hz), 7.30-7.25 (1H, m), 7.07-7.02 (1H, m), 6.84 (1H, d, J=7.7 Hz), 3.2 (3H, s), 2.91-2.84 (2H, m), 2.65-2.57 (2H, m), 2.25 (1H, d, J=7.1 Hz), 2.03-1.94 (2H, m), 1.79-1.40 (15H, m), 1.30-1.20 (2H, m)

MS (ES$^+$) m/z 341.2 (M+H)$^+$.

EXAMPLE 47

1-(methylcarbonyloxy-ethyl)-5-(cyclooctyl-methyl)-spiro[indoline-3,4'-piperidin]-2-one (Compound #46)

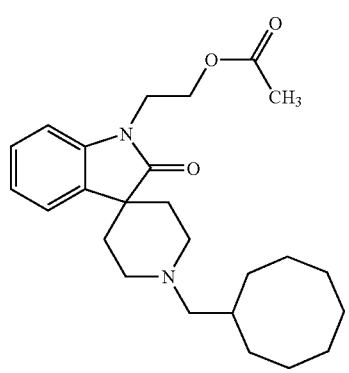

The title compound was prepared according to the procedure outlined in Example 42 above, to yield a gum.

$^1$H NMR (300 MHz, CDCl$_3$) δ 7.45 (1H, d, J=7.1 Hz), 7.29-7.23 (1H, m), 7.07-7.01 (1H, m), 6.92-6.89 (1H, m), 4.33-4.29 (2H, m), 3.98-3.94 (2H, m), 2.88-2.82 (2H, m), 2.66-2.59 (2H, m), 2.24 (1H, d, J=7.0 Hz), 2.04-1.92 (5H, m), 1.78-1.48 (15H, m), 1.29-1.23 (2H, m)

MS (ES$^+$) m/z 413.2 (M+H)$^+$.

EXAMPLE 48

1-(4-methoxy-benzyl)-5-(cyclooctyl-methyl)-spiro[indoline-3,4'-piperidin]-2-one (Compound #21)

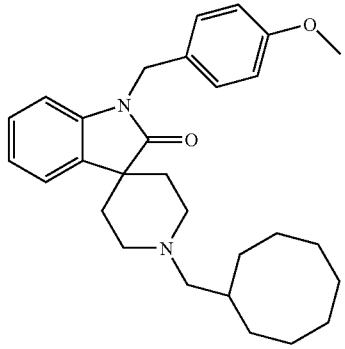

The title compound was prepared according to the procedure outlined in Example 42 above, to yield a solid.

$^1$H NMR (300 MHz, CDCl$_3$) δ 7.45 (1H, d, J=7.0 Hz), 7.21-7.12 (3H, m), 7.02-6.97 (1H, m), 6.85-6.80 (2H, m), 6.74 (1H, d, J=7.6 Hz), 4.83 (2H, s), 3.76 (3H, s), 2.93-2.86 (2H, m), 2.68-2.61 (2H, m), 2.26 (1H, d, J=7.0 Hz), 2.06-1.98 (2H, m), 1.84-1.49 (15H, m), 1.30-1.25 (2H, m)

MS (ES$^+$) m/z 447.3 (M+H)$^+$.

EXAMPLE 49

1-(hydroxyethyl)-5-(cyclooctyl-methyl)-spiro[indoline-3,4'-piperidin]-2-one (Compound #20)

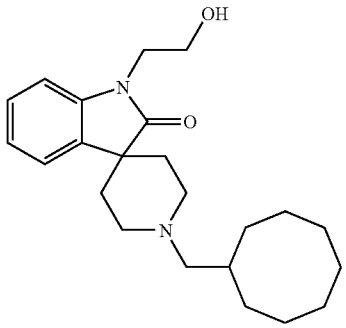

1-(methylcarbonyloxy-ethyl)-5(cyclooctyl-methyl)-spiro[indoline-3,4'-piperidin]-2-one (0.012 g, 0.028 mmol) was dissolved in methanol (1.5 mL). To the reaction mixture was then added at room temperature a 25% solution of sodium methoxide in methanol (50 μL) and the reaction mixture was stirred for 30 minutes. The solvent was evaporated in vacuo to yield an oil which was then partitioned with aqueous 0.1N HCl and dichloromethane. The organic layer was washed with brine, dried with Na$_2$SO$_4$, filtered and the solvent evaporated in vacuo to yield a crude oil. The crude oil was purified via flash chromatography (35% ethyl acetate/hexanes) to yield the title compound as an oil.

$^1$H NMR (300 MHz, CDCl$_3$) δ 7.46 (1H, d, J=7.0 Hz), 7.29-7.24 (1H, m), 7.08-7.03 (1H, m), 6.96-6.90 (1H, m), 3.95-3.85 (4H, m), 2.92-2.81 (2H, m), 2.70-2.56 (2H, m), 2.25 (1H, d, J=6.7 Hz), 2.04-1.94 (2H, m), 1.79-1.48 (15H, m), 1.30-1.23 (2H, m)

MS (ES$^+$) m/z 371.2 (M+H)$^+$.

EXAMPLE 50

1-ethyl-5-(cyclooctyl-methyl)-10-methoxy-spiro[indoline-3,4'-piperidin]-2-one (Compound #55)

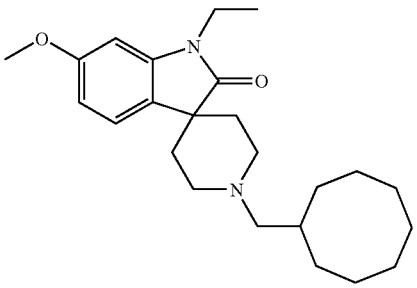

The title compound was prepared according to the procedure outlined in Example 42 above, to yield an oil.

$^1$H NMR (300 MHz, CDCl$_3$) δ 7.36 (1H, d, J=8.2 Hz), 6.52 (1H, dd, J=2.2 and 8.2 Hz), 6.44 (1H, d, J=2.2 Hz), 3.82 (3H, s), 3.77-3.70 (2H, m), 2.91-2.88 (2H, m), 2.62-2.52 (2H, m), 2.25-2.23 (2H, m), 1.99-1.93 (2H, m), 1.77-1.44 (15H, m), 1.29-1.22 (5H, m)

MS (ES$^+$) m/z 385.3 (M+H)$^+$.

EXAMPLE 51

1-methyl-5-(cyclooctyl-methyl)-10-methoxy-spiro[indoline-3,4'-piperidin]-2-one (Compound #35)

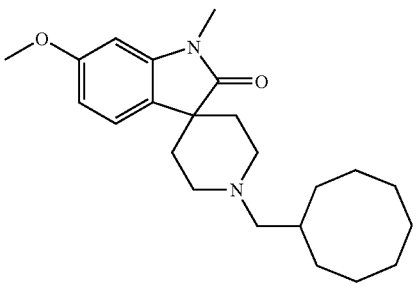

The title compound was prepared according to the procedure outlined in Example 42 above, to yield an oil.

$^1$H NMR (300 MHz, CDCl$_3$) δ 7.37 (1H, d, J=8.2 Hz), 6.54 (1H, dd, J=2.2 and 8.2 Hz), 6.43 (1H, d, J=2.2 Hz), 3.83 (3H, s), 3.17 (3H, s), 2.91-2.80 (2H, m), 2.62-2.50 (2H, m), 2.25-2.23 (2H, m), 1.99-1.94 (2H, m), 1.77-1.43 (15H, m), 1.29-1.19 (2H, m)

MS (ES$^+$) m/z 371.2 (M+H)$^+$

EXAMPLE 52

1-methyl-5-(cyclooctyl-methyl)-10-hydroxy-spiro[indoline-3,4'-piperidin]-2-one (Compound #19)

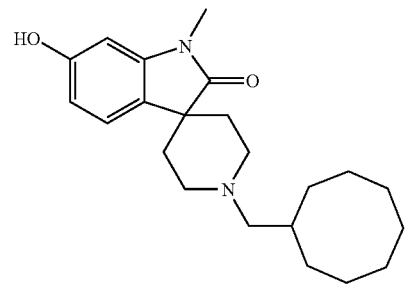

1-methyl-5-(cyclooctyl-methyl)-10-methoxy-spiro[indoline-3,4'-piperidin]-2-one (0.014 g, 0.039 mmol) was dissolved in acetic acid (0.5 mL). To the reaction mixture was then added at room temperature aqueous 48% HBr (0.5 mL) and the reaction mixture was refluxed for 48 hrs. The solvent was evaporated in vacuo to yield an oil which was then partitioned with aqueous NaHCO$_3$ and dichloromethane. The organic layer was washed with brine, dried with Na$_2$SO$_4$, filtered and the solvent evaporated in vacuo to yield the title compound as a gum.

$^1$H NMR (300 MHz, CDCl$_3$) δ7.23 (1H, d, J=8.0 Hz), 6.53-6.50 (1H, m), 6.43-6.42 (1H, m), 3.15 (3H, s), 3.12-2.98 (2H, m), 2.85-2.70 (2H, m), 2.39-2.37 (2H, m), 1.93-1.47 (17H, m), 1.38-1.25 (2H, m)

MS (ES$^+$) m/z 357.2 (M+H)$^+$

EXAMPLE 53

1-(n-propyl)-5-(cyclooctyl-methyl)-9-isopropyl-spiro[indoline-3,4'-piperidin]-2-one (Compound #17)

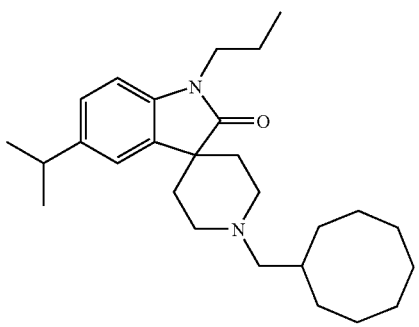

The title compound was prepared according to the procedure outlined in Example 42 above, to yield an oil.

$^1$H NMR (300 MHz, CDCl$_3$) δ7.31 (1H, d, J=1.6 Hz), 7.11 (1H, dd, J=1.6 and 8.0 Hz), 6.76 (1H, d, J=8.0 Hz), 3.66-3.61 (2H, m), 2.94-2.85 (3H, m), 2.71-2.56 (2H, m), 2.30-2.20 (2H, m), 1.98-1.90 (2H, m), 1.85-1.42 (19H, m), 1.25 (1H, d, J=6.9 Hz), 0.96-0.91 (3H, m)

MS (ES$^+$) m/z 411.2 (M+H)$^+$.

EXAMPLE 54

1-methyl-5-(cyclooctyl-methyl)-9-methyl-spiro[indoline-3,4'-piperidin]-2-one (Compound #57)

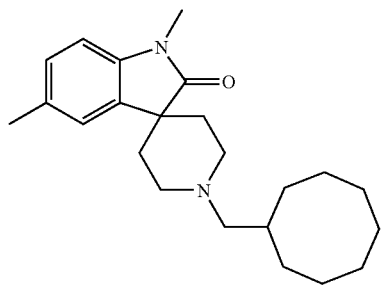

The title compound was prepared according to the procedure outlined in Example 42 above, to yield an oil.

$^1$H NMR (300 MHz, CDCl$_3$) δ 7.27-7.26 (1H, m), 7.08-7.06 (2H, m), 6.73 (1H, d, J=7.9 Hz), 3.17 (3H, s), 2.96-2.82 (2H, m), 2.69-2.55 (2H, m), 2.35 (3H, s), 2.27-2.25 (2H, m), 2.00-1.92 (2H, m), 1.82-1.45 (15H, m), 1.30-1.21 (2H, m)

MS (ES$^+$) m/z 355.3 (M+H)$^+$.

EXAMPLE 55

1-methyl-5-(cyclooctyl-methyl)-10-methyl-spiro[indoline-3,4'-piperidin]-2-one (Compound #58)

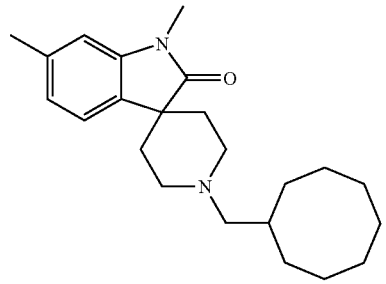

The title compound was prepared according to the procedure outlined in Example 42 above, to yield an oil.

$^1$H NMR (300 MHz, CDCl$_3$) δ 7.35 (1H, d, J=7.5 Hz), 6.86 (1H, d, J=7.5 Hz), 6.67 (1H, s), 3.18 (3H, s), 2.94-2.78 (2H, m), 2.65-2.53 (2H, m), 2.38 (3H, s), 2.29-2.17 (2H, m), 2.02-1.88 (2H, m), 1.82-1.42 (15H, m), 1.28-1.20 (2H, m)

MS (ES$^+$) m/z 355.3 (M+H)$^+$.

EXAMPLE 56

1-methyl-5-(cyclooctyl-methyl)-8-methyl-spiro[indoline-3,4'-piperidin]-2-one (Compound #59)

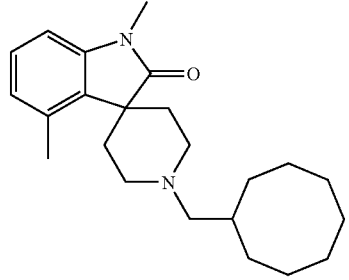

The title compound was prepared according to the procedure outlined in Example 42 above, to yield an oil.

$^1$H NMR (300 MHz, CDCl$_3$) δ 7.16 (1H, t, J=7.7 Hz), 6.82 (1H, d, J=7.7 Hz), 6.65 (1H, d, J=7.7 Hz), 3.15 (3H, s), 2.98-2.84 (2H, m), 2.79-2.62 (2H, m), 2.55-2.42 (5H, m), 2.31-2.16 (2H, m), 1.82-1.39 (15H, m), 1.34-1.20 (2H, m)

MS (ES$^+$) m/z 355.3 (M+H)$^+$.

EXAMPLE 57

1-((tetrahydropyran-2-yl)oxy-ethyl)-5-methyl-spiro[indoline-3,4'-piperidin]-2-one (Compound #2)

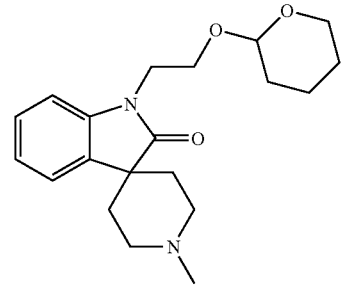

5-Methyl-spiro[indoline-3,4'-piperidin]-2-one (prepared as in Org. Prep. Proced. Int. (1995), 27(6), 691-694)(0.05 g, 0.023 mmol) was dissolved in dry N,N-dimethylformamide (4.0 mL). To the reaction mixture was then added at 0° C. sodium hydride (60% in mineral oil, 10.0 mg, 0.28 mmol)

under nitrogen atmosphere and the reaction mixture was stirred at 0° C. for one hour. To the reaction mixture was then added at 0° C. 2-(2-bromo-ethoxy)-tetrahydro-pyran (0.048 g, 0.023 mmol). The reaction mixture was stirred at 0° C. for 1 hour, then at room temperature under nitrogen atmosphere for 18 hours. The reaction mixture was then partitioned between water-ice and ethyl acetate. The organic layer was washed with brine, dried with $Na_2SO_4$, filtered and the solvent evaporated in vacuo to yield the title compound as a crude oil. The crude oil was purified via flash chromatography (3% methanol/dichloromethane) to yield the title compound as an oil.

$^1$H NMR (300 MHz, $CDCl_3$) δ7.38-7.3 (1H, m), 7.26-7.20 (1H, m), 7.05-6.97 (2H, m), 3.98-3.87 (2H, m), 3.72-3.61 (2H, m), 3.47-3.8 (1H, m), 2.97-2.89 (2H, m), 2.74-2.64 (2H, m), 2.45 (3H, s), 1.97-1.85 (4H, m), 1.73-1.42 (8H, m)

MS (ES$^+$) m/z 345.2 (M+H)$^+$.

EXAMPLE 58

1-(cyclohexyl-methyl)-5-(cyclooctyl-methyl)-spiro[indoline-3,4'-piperidin]-2-one (Compound #3)

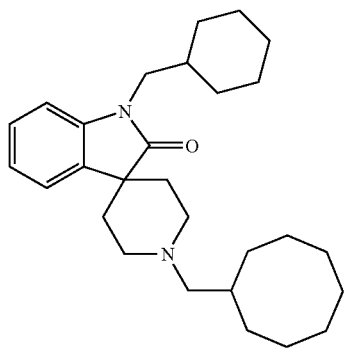

The title compound was prepared according to the procedure outlined in Example 42 above, to yield an oil.

$^1$H NMR (300 MHz, $CDCl_3$) δ 7.47-7.45 (1H, m), 7.28-7.23 (1H, m), 7.06-7.01 (1H, m), 6.86-6.83 (1H, m), 3.55-3.47 (3H, m), 3.03-2.95 (2H, m), 2.84-2.65 (2H, m), 2.42-2.6 (2H, m), 1.9-1.87 (2H, m), 1.76-1.54 (14H, m), 1.29-1.25 (3H, m), 1.23-1.08 (10H, m)

MS (ES$^+$) m/z 423.0 (M+H)$^+$.

EXAMPLE 59

1-(cyclohexyl-methyl)-5-(1-acenaphthyl)-spiro[indoline-3,4'-piperidin]-2-one (Compound #4)

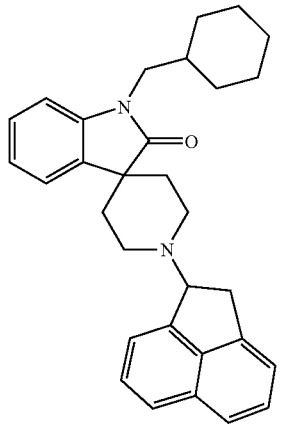

The title compound was prepared according to the procedure outlined in Example 42 above, to yield a solid.

$^1$H NMR (300 MHz, $CDCl_3$) δ 7.87-7.56(4H, m), 7.35-7.29 (4H, m), 7.7.05-7.01 (1H, m), 6.83-6.81 (1H, m), 5.76-5.73 (2H, m), 5.05-5.03 (1H, m), 3.86-3.78 (2H, m), 3.58-3.50 (2H, m), 3.29-3.23 (2H, m), 3.11-3.08 (1H, m), 1.92-1.81 (4H, m), 1.76-1.62 (10H, m)

MS (ES$^+$) m/z 451.0 (M+H)$^+$.

EXAMPLE 60

1-(cyclopropyl-methyl)-5-(cyclooctyl-methyl)-10-methoxy-spiro[indoline-3,4'-piperidin]-2-one (Compound #5)

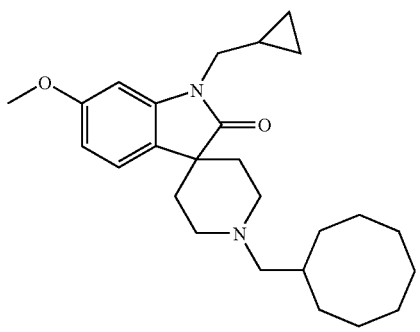

The title compound was prepared according to the procedure outlined in Example 42 above, to yield an oil.

$^1$H NMR (300 MHz, $CDCl_3$) δ 7.41-7.39 (1H, m), 6.55-6.52 (2H, m), 3.88-3.81 (2H, m), 3.83 (3H, s), 3.56-3.54 (2H, m), 1.94-1.84 (4H, m), 1.76-1.57 (4H, m), 1.55-1.44 (15H, m), 1.2-1.12 (1H, m), 0.53-0.44 (2H, m), 0.39-0.33 92H, m)

MS (ES$^+$) m/z 411.0 (M+H)$^+$.

EXAMPLE 61

1-methyl-5-(cyclooctyl-methyl)-9-isopropyl-spiro[indoline-3,4'-piperidin]-2-one (Compound #7)

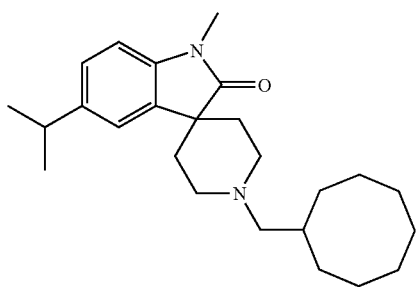

The title compound was prepared according to the procedure outlined in Example 42 above, to yield an oil.

$^1$H NMR (300 MHz, $CDCl_3$) δ7.3-7.26 (1H, m), 7.16-7.12 (1H, m), 6.79-6.74 (1H, m), 3.18 (3H, s), 2.95-2.86 (2H, m), 2.69-2.63 (1H, m), 2.26-2.25 (2H, m), 1.95-1.92 (1H, m), 1.88-1.86 (4H, m), 1.61-1.49 (14H, m), 1.27-1.24 (6H, d)

MS (ES$^+$) m/z 383.0 (M+H)$^+$.

EXAMPLE 62

1-methyl-5-(cyclooctyl-methyl)-9-trifluoromethyl-spiro[indoline-3,4'-piperidin]-2-one (Compound #8)

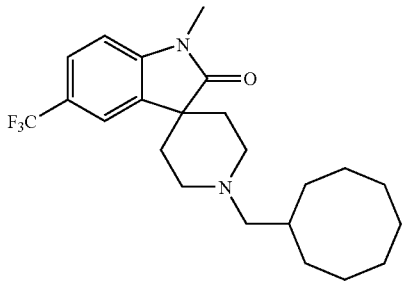

The title compound was prepared according to the procedure outlined in Example 42 above, to yield an oil.

$^1$H NMR (300 MHz, CDCl$_3$) δ 7.8 (1H, s), 7.58-7.50 (1H, m), 6.85-6.84 (1H, m), 3.16 (3H, s), 2.89-2.82 (2H, m), 2.79-2.59 (2H, m), 2.2-2.18 (2H, m), 1.97-1.92 (1H, m), 1.8-1.71 (4H, m), 1.64-1.42 (14H, m)

MS (ES$^+$) m/z 409.0 (M+H)$^+$.

EXAMPLE 63

1-methyl-5-(cyclooctyl-methyl)-9-fluoro-spiro[indoline-3,4'-piperidin]-2-one (Compound #9)

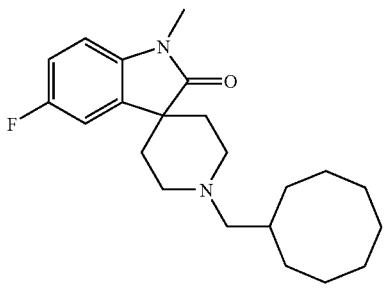

The title compound was prepared according to the procedure outlined in Example 42 above, to yield a foam.

$^1$H NMR (300 MHz, CDCl$_3$) δ 7.26-7.21 (1H, m), 7.01-6.97 (1H, m), 6.77-6.72 (1H, m), 3.19 (3H, s), 2.75-2.62 (2H, m), 2.42-2.29 (2H, m), 2.07-1.96 (2H, m), 1.76-1.68 (4H, m), 1.61-1.38 (15H, m)

MS (ES$^+$) m/z 359.0 (M+H)$^+$.

EXAMPLE 64

1-(methylcarbonyloxy-methyl)-5-(4-trifluoromethyl-benzyl)-spiro[indoline-3,4'-piperidin]-2-one (Compound #11)

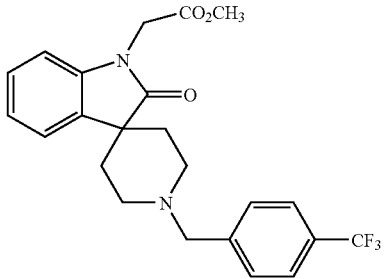

The title compound was prepared according to the procedure outlined in Example 43 above, to yield a solid.

$^1$H NMR (300 MHz, CDCl$_3$) δ 7.62-7.59 (2H, m), 7.56-7.51 (2H, m), 7.41-7.38 (1H, m), 7.28-7.23 (1H, m), 7.11-7.04 (1H, m), 6.72-6.68 (1H, m), 4.45 (2H, s), 3.73 (3H, s), 3.68 (2H, s), 2.97-2.92 (2H, m), 2.74-2.67 (2H, m), 2.01-1.98 (4H, m)

MS (ES$^+$) m/z 433.0 (M+H)$^+$.

EXAMPLE 65

1-(methylcarbonyloxy-methyl)-5-(3-trifluoromethyl-benzyl)-spiro[indoline-3,4'-piperidin]-2-one (Compound #12)

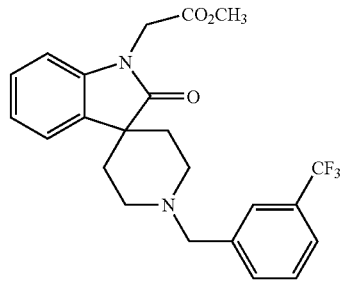

The title compound was prepared according to the procedure outlined in Example 43 above, to yield a solid.

$^1$H NMR (300 MHz, CDCl$_3$) δ 7.68-7.63 (1H, m) 7.61-7.58 (1H, m), 7.52-7.49 (1H, m), 7.45-7.38 (2H, m), 7.27-7.19 (1H, m), 7.09-7.03 (1H, m), 6.72-6.67 (1H, m), 4.46 (2H, s), 3.72 (3H, s), 3.70 (2H, s), 2.98-2.87 (2H, m), 2.74-2.64 (2H, m), 2.05-1.87 (4H,m)

MS (ES$^+$) m/z 433.0 (M+H)$^+$.

EXAMPLE 66

1-(methylcarbonyloxy-methyl)-5-(4-biphenyl-methyl)-spiro[indoline-3,4'-piperidin]-2-one (Compound #13)

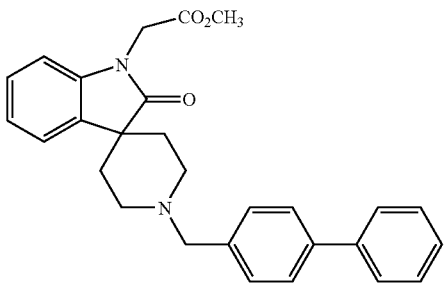

The title compound was prepared according to the procedure outlined in Example 43 above, to yield a solid.

$^1$H NMR (300 MHz, CDCl$_3$) δ 7.61-7.57 (4H, m), 7.52-7.38 (2H, m), 7.35-7.32 (1H, m), 7.29-7.22 (4H, m), 7.12-7.06 (1H, m), 6.73-6.67 (1H, m), 4.40 (2H, s), 3.92 (2H, s), 3.71 (3H, s), 3.2-2.84 (4H, m), 2.09-2.02 (2H, m), 2.00-1.97 (2H, m)

MS (ES$^+$) m/z 441.0 (M+H)$^+$.

EXAMPLE 67

1-(oxarinyl-methyl)-5-(cyclooctyl-methyl)-spiro[indoline-3,4'-piperidin]-2-one (Compound #60)

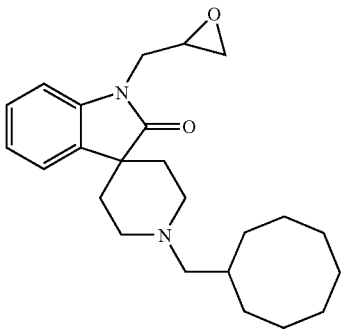

5-(Cyclooctyl-methyl)-spiro[indoline-3,4'-piperidin]-2-one (0.075 g, 0.231 mmol) was dissolved in N,N-dimethylformamide (5 mL). To the reaction mixture was then added at 0° C. sodium hydride (60% in mineral oil, 0.028 g, 0.69 mmol) under nitrogen atmosphere. The reaction mixture was stirred at 0° C. for 40 minutes. To the reaction mixture was then added epichlorhydrin (0.075 g, 0.808 mmol). The reaction mixture was stirred at 0° C. for one hour, then for 18 hours at room temperature under nitrogen atmosphere. The reaction mixture was then partitioned with water and ethyl acetate. The organic layer was dried with $Na_2SO_4$, filtered and the solvent evaporated in vacuo to yield a crude oil. The crude oil was purified via flash chromatography (3% methanol/dichloromethane) to yield the title compound as a foam.

$^1$H NMR (300 MHz, $CDCl_3$) δ 7.45 (1H, d, J=7.1 Hz), 7.30-7.24 (1H, m), 7.08-702 (2H, m), 4.22 (1H, dd, J=3.1 and 15.0 Hz), 3.61 (1H, dd, J=5.5 and 15.0 Hz), 3.28-3.14 (1H, m), 2.95-2.80 (3H, m), 2.83-2.62 (3H, m), 2.27-2.24 (2H, m), 1.98-1.92 (2H, m), 1.80-1.39 (15H, m), 1.26-1.22 (2H, m)

MS ($ES^+$) m/z 383.2 $(M+H)^+$.

EXAMPLE 68

1-(3-(4-morpholinyl-ethyl-amino)-2-hydroxy-n-propyl)-5-(cyclooctyl-methyl)-spiro[indoline-3,4'-piperidin]-2-one (Compound #61)

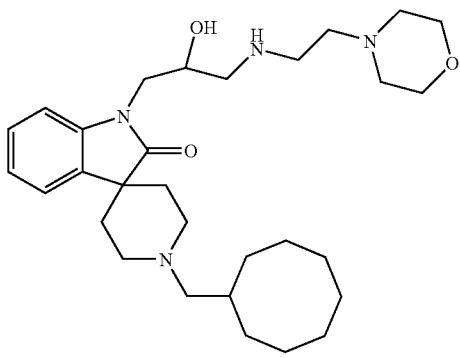

1-(Oxarinyl-methyl)-5-(cyclooctyl-methyl)-spiro[indoline-3,4'-piperidin]-2-one (0.01 g, 0.026 mmol) was dissolved in absolute ethanol (0.6 mL), mixed with 2-morpholin-4-yl-ethylamine (10.4 mg, 0.079 mmol) and heated under stirring at 70° C. overnight. The solvent was evaporated and the resulting residue was purified via flash chromatography (4.0% ammonia 2.0 M in methanol/dichloromethane) to yield the title compound as an oil.

$^1$H NMR (300 MHz, $CDCl_3$) δ 7.44 (1H, d, J=7.3 Hz), 7.29-7.23 (1H, m), 7.07-7.02 (2H, m), 3.94-3.86 (2H, m), 3.72-3.62 (5H, m), 2.89-2.81 (2H, m), 2.76-2.59 (6H, m), 2.54-2.36 (7H, m), 2.24 (1H, d, J=7.1 Hz), 1.98 (2H, m), 1.82-1.48 (15H, m), 1.29-1.20 (2H, m)

MS ($ES^+$) m/z 513.4 $(M+H)^+$.

EXAMPLE 69

1-[(2R-methylcarbonylamino-2-carboxy-ethyl)-thio-(2-hydroxy-n-propyl)]-5-(cyclooctyl-methyl)-spiro[indoline-3,4'-piperidin]-2-one (Compound #16)

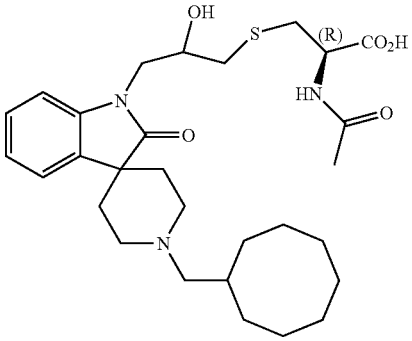

1-(Oxarinyl-methyl)-5-(cyclooctyl-methyl)-spiro[indoline-3,4'-piperidin]-2-one (0.009 g, 0.023 mmol) was dissolved in absolute ethanol (0.6 mL), mixed with N-acetyl-L-cysteine (11.5 mg, 0.070 mmol) and heated under stirring at 70° C. overnight. The solvent was evaporated and the resulting residue was purified via flash chromatography (4.0% ammonia 2.0 M in methanol/dichloromethane) to yield the title compound as an oil.

$^1$H NMR (300 MHz, $CDCl_3$) δ 7.46 (1H, d, J=7.2 Hz), 7.31-7.26 (1H, m), 7.10-6.91 (2H, m), 6.44 (1H, bs), 4.89-4.79 (1H, m), 4.31-4.15 (2H, m), 3.95-3.75 (2H, m), 3.05-2.96 (2H, m), 2.88-2.73 (2H, m), 2.66-2.56 (2H, m), 2.25-2.23 (2H, m), 2.09 (3H, s), 2.07-1.94 (2H, m), 1.85-1.48 (15H, m), 1.28-1.22 (2H, m)

MS ($ES^+$) m/z 546.3 $(M+H)^+$.

EXAMPLE 70

1-[2-hydroxy-3-(N-ethyl-N-(4-methylbenzyl)-amino)-n-propyl]-5-(cyclooctyl-methyl)-spiro[indoline-3,4'-piperidin]-2-one (Compound #62)

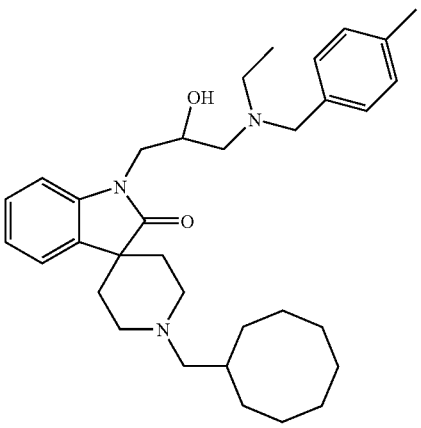

1-(Oxarinyl-methyl)-5-(cyclooctyl-methyl)-spiro[indoline-3,4'-piperidin]-2-one. (0.01 g, 0.026 mmol) was dissolved in absolute ethanol (0.6 mL), mixed with methyl-(4-methyl-benzyl)-amine (11.7 mg, 0.078 mmol) and heated under stirring at 70° C. overnight. The solvent was evaporated and the resulting residue was purified via flash chromatography (5% methanol/dichloromethane) to yield the title compound as an oil.

$^1$H NMR (300 MHz, CDCl$_3$) δ 7.42 (1H, d, J=6.7 Hz), 7.27-7.22 (1H, m), 7.13-7.01 (6H, m), 3.95-3.60 (4H, m), 3.44-3.39 (1H, m), 2.90-2.78 (2H, m), 2.67-2.54 (4H, m), 2.53-2.40 (4H, m), 2.30 (3H, m), 2.29-2.19 (2H, m), 1.92-1.39 (15H, m), 1.32-1.18 (2H, m), 1.04-0.99 (3H, t, J=7.1 Hz)

MS (ES$^+$) m/z 532.3 (M+H)$^+$.

EXAMPLE 71

1-ethyl-10-methoxy-spiro[indoline-3,4'-piperidin]-2-one

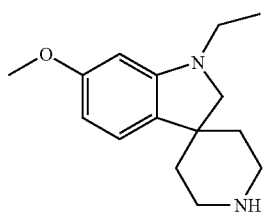

1-Ethyl-10-methoxy-spiro[indoline-3,4'-piperidin]-2-one (0.048 g, 0.184 mmol) was dissolved in dry THF (3.5 mL). To the reaction mixture was then added at 0° C. a solution of lithium aluminium hydride 1.0 in THF (4.6 mL, 4.6 mmol) under nitrogen atmosphere. The reaction mixture was refluxed for 4 hrs, cooled down to room temperature, then cooled 0° C. To the reaction mixture was then added aqueous NH$_4$Cl. The reaction mixture was filtered and partitioned with water and ethyl acetate. The organic layer was dried with Na$_2$SO$_4$, filtered and the solvent evaporated in vacuo to yield a crude oil. The crude oil was purified via flash chromatography (15% ammonia 2.0 M in methanol/dichloromethane) to yield the title compound as a solid.

$^1$H NMR (300 MHz, CDCl$_3$) δ 6.93 (1H, d, J=8.0 Hz), 6.19 (1H, dd, J=2.2 and 8.0 Hz), 6.04 (1H, d, J=2.2 Hz), 3.76 (3H, s), 3.27 (3H, s), 3.18-3.06 (4H, m), 2.76-2.72 (2H, m), 2.34 (1H, bs), 1.84-1.65 (4H, m), 1.16 (3H, t, J=7.2 Hz)

MS (ES$^+$) m/z 247.0 (M+H)$^+$.

EXAMPLE 72

1-ethyl-5-(cyclooctyl-methyl)-10-methoxy-spiro[indoline-3,4'-piperidine (Compound #55)

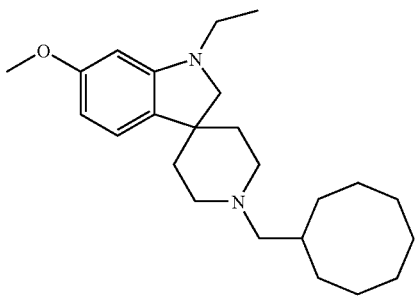

1-Bromomethyl-cyclooctane (0.027 g, 0.129 mmol) and 1-ethyl-5-(cyclooctyl-methyl)-10-methoxy-spiro[indoline-3,4'-piperidine] (0.01 g, 0.043 mmol) were dissolved in dry N,N-dimethylformamide (2 mL). Potassium carbonate (0.024 g, 0.172 mmol) and a catalytic amount of potassium iodide were added and the reaction mixture was stirred at 60° C. under nitrogen atmosphere for 18 hours. The reaction mixture was partitioned with water and ethyl acetate. The organic layer was washed with brine, dried with Na$_2$SO$_4$, filtered and the solvent evaporated in vacuo to yield a crude oil. The crude oil was purified via flash chromatography (3.5% methanol/dichloromethane) to yield the title compound as an oil.

$^1$H NMR (300 MHz, CDCl$_3$) δ 6.94 (1H, d, J=8.0 Hz), 6.18 (1H, dd, J=2.2 and 8.0 Hz), 6.03 (1H, d, J=2.2 Hz), 3.76 (3H, s), 3.22 (2H, s), 3.17-3.10 (2H, m), 2.82-2.78 (2H, m), 2.11-1.85 (6H, m), 1.78-1.41 (15H, m), 1.28-1.21 (2H, m), 1.16 (3H, t, J=7.2 Hz)

MS (ES$^+$) m/z 371.0 (M+H)$^+$.

EXAMPLE 73

1-(methylcarbonyloxy-methyl)-5-(phenyl-carbonyl-ethyl-carbonyl)-spiro[indoline-3,4'-piperidin]-2-one (Compound #31)

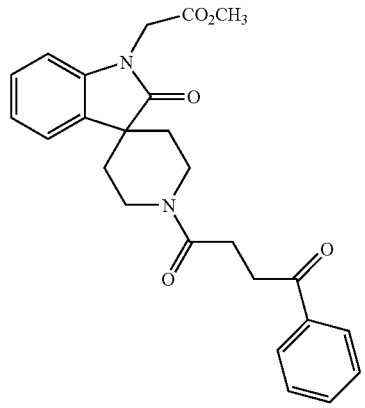

4-Oxo-4-phenyl-butyric acid (0.010 g, 0.058 mmol) was suspended in dry dichloromethane (2 mL). 1-(3-Dimethylaminopropyl)-3-ethylcarbodiimide HCl salt (0.017 g, 0.087 mmol) and dimethyl-pyridin-4-yl-amine (0.014 g, 0.1166 mmol) were then added and the reaction mixture was refluxed for 30 minutes. A solution of 1-(methoxycarbonyl-methyl)-spiro[indoline-3,4'-piperidin]-2-one (0.016 g, 0.058 mmol) in dry dichloromethane was added under nitrogen atmosphere and the reaction mixture was refluxed for 18 hrs, then cooled to room temperature. The reaction mixture was then washed with aqueous 0.5M citric acid, aqueous NaHCO$_3$, brine, dried with Na$_2$SO$_4$, filtered and the solvent evaporated in vacuo to yield a crude oil. The crude oil was purified via flash chromatography (3% methanol/dichloromethane) to yield the title compound as a solid.

$^1$H NMR (300 MHz, CDCl$_3$) δ 8.02-7.97 (2H, m), 7.57-7.53 (1H, m), 7.49-7.42 (2H, m), 7.29-7.23 (2H, m), 7.10-7.06 (1H, m), 6.74-6.70 (1H, m), 4.48 (2H, s), 4.33-4.26 (1H, m), 4.12-4.07 (1H, m), 3.92-3.77 (5H, m), 3.58-3.48 (1H, m), 3.38-3.28 (1H, m), 3.0-2.91 (1H, m), 2.86-2.75 (1H, m), 2.03-1.84

MS (ES$^+$) m/z 435.0 (M+H)$^+$.

EXAMPLE 74

1-(methylcarbonyloxy-methyl)-5-(4-t-butyl-cyclohexyl-methyl)-spiro[indoline-3,4'-piperidin]-2-one (Compound #29)

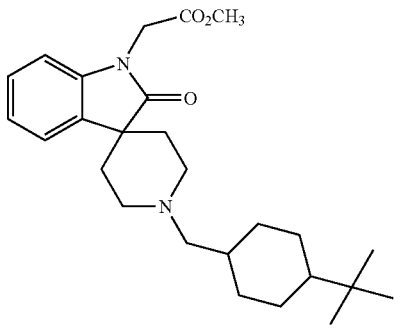

1-(Methoxycarbonyl-methyl)-spiro[indoline-3,4'-piperidin]-2-one (0.0137 g, 0.049 mmol) and 4-tert-butyl-cyclohexanecarbaldehyde (0.01 g, 0.06 mmol) were dissolved in dry 1,2-dichloroethane (1.5 mL). To the reaction mixture was then added glacial acetic acid (0.003 g, 0.049 mmol) under nitrogen atmosphere and the reaction mixture was stirred at room temperature for 30 minutes. To the reaction mixture was then added, at room temperature, sodium triacetoxyborohydride (0.018 g, 0.084 mmol) under nitrogen atmosphere and the reaction mixture was stirred at room temperature for 18 hours. The reaction mixture was then partitioned with aqueous NaHCO$_3$ and dichloromethane. The organic layer was washed with brine, dried with Na$_2$SO$_4$, filtered and the solvent evaporated in vacuo to yield a crude oil. The crude oil was purified via flash chromatography (4.5% ammonia 2.0 M in methanol/dichloromethane) to yield the title compound as an oil.

$^1$H NMR (300 MHz, CDCl$_3$) δ 7.44 (1H, d, J=7.1 Hz), 7.27-7.22 (1H, m), 7.09-7.04 (1H, m), 6.71 (1H, d, J=7.7 Hz), 4.46 (2H, s), 3.74 (3H, s), 2.95-2.81 (2H, m), 2.72-2.58 (2H, m), 2.36-2.24 (2H, m), 2.02-0.91 (14H, m), 0.84 (9H, s)

MS (ES$^+$) m/z 427.3 (M+H)$^+$.

EXAMPLE 75

1-(methylcarbonyloxy-methyl)-5-(5-n-undecanoyl)-spiro[indoline-3,4'-piperidin]-2-one (Compound #28)

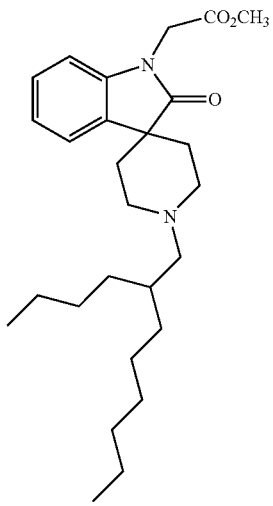

The title compound was prepared according to the procedure outlined in Example 42 above, to yield an oil.

$^1$H NMR (300 MHz, CDCl$_3$) δ 7.49-7.47 (1H, m), 7.28-7.22 (1H, m), 7.10-7.05 (1H, m), 6.72 (1H, d, J=7.7 Hz), 4.46 (2H, s), 3.74 (3H, s), 2.92-2.81 (2H, m), 2.71-2.55 (2H, m), 2.38-2.24 (2H, m), 2.04-1.78 (4H, m), 1.41-1.14 (16H, m), 0.93-0.85 (6H, m)

MS (ES$^+$) m/z 443.4 (M+H)$^+$.

EXAMPLE 76

1-(methylcarbonyloxy-methyl)-5-(n-hexyl)-spiro[indoline-3,4'-piperidin]-2-one (Compound #26)

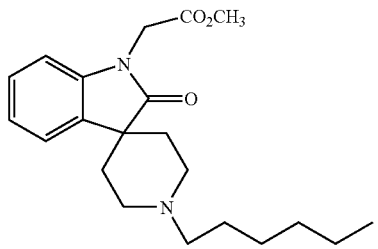

The title compound was prepared according to the procedure outlined in Example 43 above, to yield an oil.

$^1$H NMR (300 MHz, CDCl$_3$) δ 7.39 (1H, d, J=7.4 Hz), 7.28-7.21 (1H, m), 7.10-7.04 (1H, m), 6.71 (1H, d, J=7.7 Hz), 4.46 (2H, s), 3.74 (3H, s), 2.97-2.89 (2H, m), 2.77-2.70 (2H, m), 2.53-2.48 (2H, m), 1.98-1.95 (3H, m), 1.78-1.31 (9H, m), 0.92-0.87 (3H, m)

MS (ES$^+$) m/z 359.2 (M+H)$^+$

EXAMPLE 77

1-(methylcarbonyloxy-methyl)-5-(4-methoxy-cyclohexyl-cabonyl)-spiro[indoline-3,4'-piperidin]-2-one (Compound #22)

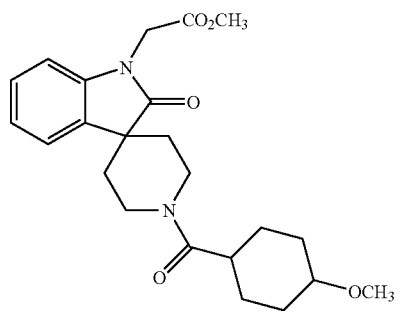

4-Methoxy-cyclohexanecarboxylic acid (0.006 g, 0.036 mmol) was suspended in dry dichloromethane (1 mL) and dry N,N-dimethylformamide (0.05 mL). 1-(3-dimethylamino-propyl)-3-ethylcarbodiimide HCl salt (0.005 g, 0.04 mmol) and 1-hydroxybenzotriazole hydrate (0.006 g, 0.047 mmol) were added and the reaction mixture was stirred under nitrogen atmosphere at room temperature for 30 minutes. A solution of 1-(methoxycarbonyl-methyl)-spiro[indoline-3,4'-piperidin]-2-one (0.010 g, 0.036 mmol) in dry dichloromethane (1 mL) was added under nitrogen atmosphere and the reaction mixture was stirred under nitrogen atmosphere at room temperature for 18 hrs. The reaction mixture was then partitioned with water and dichloromethane. The organic layer was washed with aqueous NaHCO$_3$, aqueous 0.5 N HCl, brine, dried with Na$_2$SO$_4$, filtered and the solvent evaporated in vacuo to yield a crude oil. The crude oil was purified via flash chromatography (4% ammonia 2.0 M in methanol/dichloromethane) to yield the title compound as an oil.

¹H NMR (300 MHz, CDCl₃) δ7.28-7.24 (2H, m), 7.12-7.09 (1H, m), 6.74 (1H, d, J=7.7 Hz), 4.48 (2H, s), 4.30-4.22 (2H, m), 4.06-3.97 (2H, m), 3.82-3.73 (5H, m), 3.37 (3H, s), 3.22-3.13 (1H, m), 2.57-2.47 (1H, m), 2.20-2.16 (2H, m), 1.96-1.78 (5H, m), 1.75-1.68 (1H, m), 1.29-1.18 (4H, m)
MS (ES⁺) m/z 415.1 (M+H)⁺.

EXAMPLE 78

1-carboxymethyl)-5-(cyclooctyl-methyl)-spiro[indoline-3,4'-piperidin]-2-one (Compound #41)

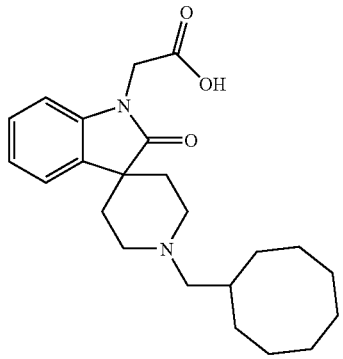

To 1-(methylcarbonyloxy-methyl)-5-(cyclooctyl-methyl)-spiro[indoline-3,4'-piperidin]-2-one (0.026 g, 0.065 mmol) in a mixture of THF/water/methanol (1 mL/0.5 mL/0.5 mL) was added lithium hydroxide (0.0068 g, 0.163 mmol) at 0° C. and the reaction mixture was stirred at 0° C. for 3 hours. The reaction mixture was then partitioned with aqueous 3N HCl and dichloromethane. The organic layer was dried with N₂SO₄, filtered and the solvent evaporated in vacuo to yield the title compound as a solid.
¹H NMR (300 MHz, CDCl₃) δ 12.2-12.05 (1H, m), 7.45-7.32 (1H, m), 7.26-7.18 (1H, m), 7.08-7.03 (1H, m), 6.75-6.73 (1H, m), 3.78-3.49 (2H, m), 3.40-3.37 (2H, m), 3.14-3.05 (2H, m), 2.89-2.87 (2H, m), 2.11-2.04 (1H, m), 1.72-1.61 (4H,m), 1.54-1.43 (14H, m)
MS (ES⁺) m/z 385.3 (M+H)⁺.

EXAMPLE 79

1-(methylcarbonyloxy-methyl)-5-(phenyl-ethyl)-spiro[indoline-3,4'-piperidin]-2-one (Compound #37)

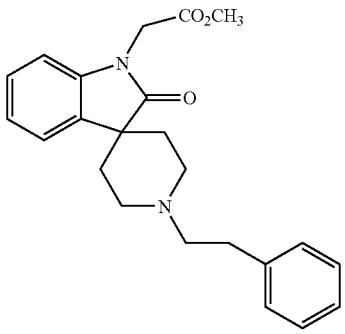

The title compound was prepared according to the procedure outlined in Example 43 above, to yield a solid.
¹H NMR (300 MHz, CDCl₃) δ7.43-7.38 (1H, m), 7.31-7.29 (6H, m), 7.13-7.06 (1H, m), 6.6.73-6.68 (1H, m), 4.46 (2H, s), 3.75 (3H, s), 3.08-2.92 (2H, m), 2.90-2.83 (2H, m), 2.80-2.71 (4H, m), 2.08-1.91 (4H, m),
MS (ES⁺) m/z 379.1 (M+H)⁺.

EXAMPLE 80

1-(methylcarbonyloxy-methyl)-2-(2-naphthyl-methyl)-spiro[indoline-3,4'-piperidin]-2-one (Compound #32)

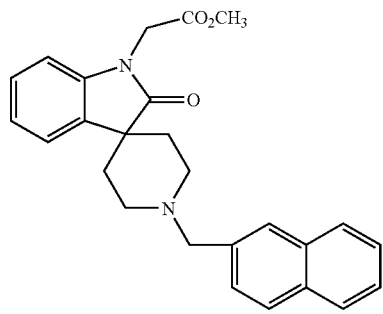

The title compound was prepared according to the procedure outlined in Example 43 above, to yield a solid.
¹H NMR (300 MHz, CDCl₃) δ 7.84-7.81 (4H, m), 7.59-7.56 (1H, m), 7.48-7.42 (3H, m), 7.29-7.24 (1H, m), 7.1-7.05 (1H, m), 6.72-6.70 (1H, m), 4.47 (2H, s), 3.83 (2H, s), 3.74 (3H, s), 2.98-2.95 (2H, m), 2.79-2.75 (2H, m), 2.04-1.92 (4H, m)
MS (ES⁺) m/z 415.1 (M+H)⁺.

EXAMPLE 81

1-(methylcarbonyloxy-methyl)-5-(1-acenaphthyl)-spiro[indoline-3,4'-piperidin]-2-one (Compound #30)

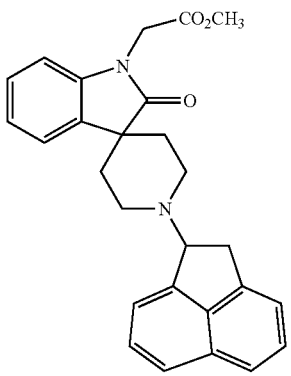

1-Bromo-acenaphthene (0.022 g, 0.093 mmol) and 1-(methoxycarbonylmethyl)-spiro[indoline-3,4'-piperidin]-2-one (0.013 g, 0.046 mmol) were dissolved in dry N,N-dimethylformamide (1 mL). Potassium carbonate (0.02 g, 0.14 mmol) was then added and the reaction mixture was stirred at room temperature under a nitrogen atmosphere for 18 hours. The reaction mixture was partitioned with water and ethyl acetate. The organic layer was washed with brine, dried with Na₂SO₄, filtered and the solvent evaporated in vacuo to yield a crude oil. The crude oil was purified via flash chromatography (5% methanol/dichloromethane) to yield the title compound as a foam.
¹H NMR (300 MHz, CDCl₃) δ 7.7-7.69 (1H, m), 7.68-7.59 (2H, m), 7.50-7.28 (4H, m), 7.27-7.23 (1H, m), 7.13-7.07 (1H, m), 6.75-6.71 (1H, m), 5.06-5.04 (1H, m), 4.44 (2H, s), 3.72 (3H, s), 3.24-3.07 (2H, m), 2.89-2.85 (2H, m), 2.61-2.57 (1H, m), 1.98-1.79 (5H, m), 1.61-1.50 (1H, m)
MS (ES⁺) m/z 427.0 (M+H)⁺.

EXAMPLE 82

1-(methylcarbonyloxy-methyl)-5-(2-decahydronaph-thyl)-spiro[indoline-3,4'-piperidin]-2-one (Compound #15)

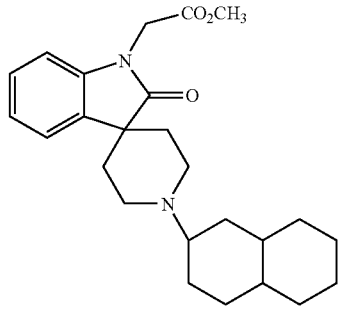

1-(Methoxycarbonylmethyl)-spiro[indoline-3,4'-piperidin]-2-one (0.013 g, 0.049 mmol) was dissolved in dry THF (1.0 mL) and dry 1,2-dichloroethane (0.3 mL). Octahydronaphthalen-2-one (0.008 g, 0.054 mmol), glacial acetic acid (0.003 g, 0.049 mmol), MP-cyanoborohydride (Polymer support from Argonaut) (0.043 g, 0.099 mmol) were added and the reaction mixture was stirred at room temperature for 18 hrs. The mixture was then filtered, the resin washed with dichloromethane and the solvent evaporated in vacuo to yield the crude compound. The crude compound was purified via flash chromatography (5% methanol/dichloromethane) to yield the title compound as a foam.

$^1$H NMR (300 MHz, CDCl$_3$) δ7.47-7.44 (1H, m), 7.28-7.23 (1H, m), 7.17-7.08 (1H, m), 6.73-6.71 (1H, m), 4.45 (2H, s), 3.76 (3H, s), 3.62-3.37 (2H, m), 3.28-3.11 (2H, m), 2.31-2.12 (1H, m), 2.02-1.83 (4H, m), 1.72-1.05 (16H, m)

MS (ES$^+$) m/z 411.2 (M+H)$^+$.

EXAMPLE 83

1-(methylcarbonyloxy-methyl)-5-(cyclododecyl-methyl)-spiro[indoline-3,4'-piperidin]-2-one (Compound #27)

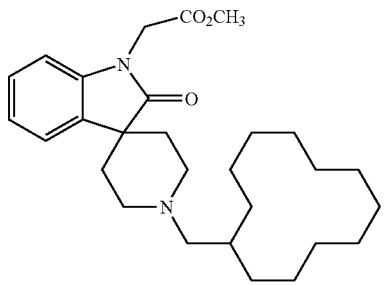

The title compound was prepared according to the procedure outlined in Example 44 above, to yield an oil.

$^1$H NMR (300 MHz, CDCl$_3$) δ7.49-7.47 (1H, m), 7.29-7.22 (1H, m), 7.10-7.05 (1H, m), 6.73-6.71 (1H, m), 4.46 (2H, s), 3.75 (3H, s), 2.85-2.78 (2H, m), 2.72-2.51 (2H, m), 2.39-2.34 (2H, m), 2.06-1.98 (2H, m), 1.85-1.67 (2H, m), 1.59-1.41 (1H,m), 1.35-1.25 (18H,m)

MS (ES$^+$) m/z 455.4 (M+H)$^+$

EXAMPLE 84

1-(methylcarbonyloxy-methyl)-5-(2-(1,2,3,4-tetrahy-dronaphthyl))-spiro[indoline-3,4'-piperidin]-2-one (Compound #25)

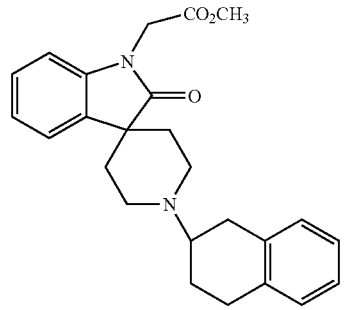

The title compound was prepared according to the procedure outlined in Example 82 above, to yield an oil.

$^1$H NMR (300 MHz, CDCl$_3$) δ7.42-7.39 (1H, m), 7.28-7.22 (2H,m), 7.13-7.09 (4H, m), 6.74-6.71 (1H,m), 4.47 (2H, s), 3.75 (3H, s), 3.35-3.24 (2H, m), 3.05-2.85 (6H, m), 2.24-2.19 (1H, m), 2.11-1.91 (4H, m), 1.86-1.77 (2H, m)

MS (ES$^+$) m/z 405.2 (M+H)$^+$

EXAMPLE 85

1-(methylcarbonyloxy-methyl)-5-(cyclohexyl-methyl)-spiro[indoline-3,4'-piperidin]-2-one (Compound #24)

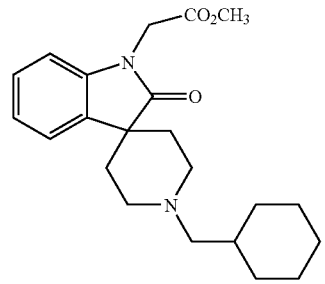

The title compound was prepared according to the procedure outlined in Example 43 above, to yield an oil.

$^1$H NMR (300 MHz, CDCl$_3$) δ 7.45-7.43 (1H, m), 7.28-7.21 (2H, m), 7.09-7.04 (1H, m), 6.72-6.70 (1H, m), 4.46 (2H, s), 3.74 (3H, s), 2.94-2.81 (2H, m), 2.73-2.61 (2H, m), 2.34-2.27 (1H, m), 2.08-1.85 (4H, m), 1.82-1.54 (6H, m), 1.27-1.12 (4H,m), 1.02-0.87 (2H,m)

MS (ES$^+$) m/z 371.2 (M+H)$^+$

EXAMPLE 86

1-(methylcarbonyloxy-methyl)-5-(cyclopropyl-methyl)-spiro[indoline-3,4'-piperidin]-2-one (Compound #23)

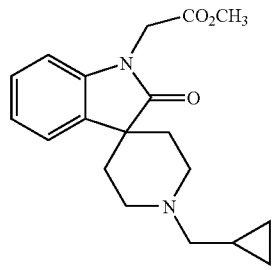

The title compound was prepared according to the procedure outlined in Example 43 above, to yield an oil.

$^1$H NMR (300 MHz, CDCl$_3$) δ7.40-7.37 (1H, m), 7.28-7.22(1H, m), 7.10-7.05 (1H, m), 6.73-6.71 (1H, m), 4.46 (2H, s), 3.74 (3H, s), 3.02-2.92 (2H, m), 2.88-2.81 (2H, m), 2.47-2.45 (2H, m), 2.07-1.94 (4H, m), 1.44-0.97 (1H, m), 0.59-0.52 (2H,m), 0.18-0.16 (2H,m)

MS (ES$^+$) m/z 329.2 (M+H)$^+$

EXAMPLE 87

1-(methylcarbonyloxy-methyl)-5-(1-naphthyl-methyl)-spiro[indoline-3,4'-piperidin]-2-one (Compound #43)

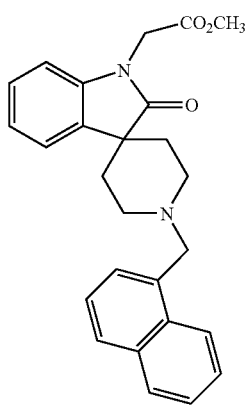

The title compound was prepared according to the procedure outlined in Example 43 above, to yield a solid.

$^1$H NMR (300 MHz, CDCl$_3$) δ 8.41-8.37 (1H,m), 7.88-7.83 (1H, m), 7.81-7.76(1H, m), 7.54-7.41 (5H, m), 7.26-7.23 (1H, m), 7.11-7.06 (1H,m), 6.72-6.68 (1H,m), 4.46 (2H, s), 4.08 (2H,s), 3.74 (3H, s), 3.04-2.94 (2H, m), 2.83-2.75 (2H, m), 2.02-1.94 (2H, m), 1.91-1.82 (2H, m)

MS (ES$^+$) m/z 415.1(M+H)$^+$

EXAMPLE 88

1-(methylcarbonyloxy-methyl)-5-(2-(3-thienyl)-benzyl)-spiro[indoline-3,4'-piperidin]-2-one (Compound #40)

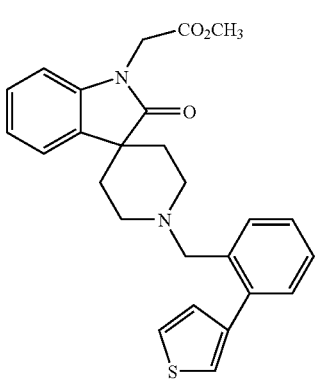

The title compound was prepared according to the procedure outlined in Example 43 above, to yield an oil.

$^1$H NMR (300 MHz, CDCl$_3$) δ 7.61-7.52 (2H,m), 7.46-7.24 (7H, m), 7.10-7.04 (1H, m), 6.73-6.68 (1H, m), 4.46 (2H, s), 3.74 (3H, s), 3.61 (2H.s), 2.97-2.87 (2H, m), 2.74-2.65 (2H, m), 2.04-1.94 (2H, m), 1.89-1.78 (2H, m)

MS (ES$^+$) m/z 447.1(M+H)$^+$

EXAMPLE 89

5-methyl-spiro[indoline-3,4'-piperidin]-2-one (Compound #36)

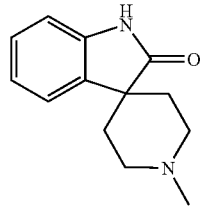

The title compound was prepared according to the procedure outlined in Org. Prep. Proced. Int. (1995) 27(6), 691-694, to yield a solid.

$^1$H NMR (300 MHz, CDCl$_3$) δ 7.88-7.82 91H,m), 7.38-7.33 (1H,m), 7.27-7.17 (1H, m), 7.06-6.98 (1H, m), 6.89-6.83 (1H, m), 3.12-2.95 (2H, m), 2.87-2.74 (2H, m), 2.51 (3H, s), 2.18-2.03 (2H, m), 1.99-1.89 (2H,m)

MS (ES$^+$) m/z 217.1(M+H)$^+$

EXAMPLE 90

1-(hydroxyethyl)-5-tert-butoxycarbonyl-spiro[indoline-3,4'-piperidin]-2-one (Compound #52)

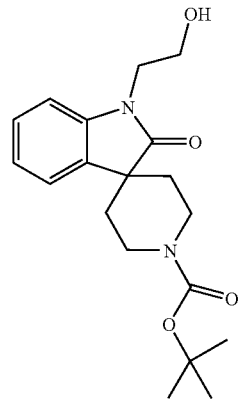

1-(Tetrahydropyran-2-yl-oxy-ethyl)-5-tert-butoxycarbonyl-spiro[indoline-3,4'-piperidin]-2-one (0.021 g, 0.05 mmol) was dissolved in methanol (2 mL). To the reaction mixture was then added at room temperature aqueous 1.0N HCl (80 μL) and the reaction mixture was stirred for 30 minutes. The reaction mixture was then partitioned with aqueous Na$_2$CO$_3$ and ethyl acetate. The organic layer was washed with brine, dried with Na$_2$SO$_4$, filtered and the solvent evaporated in vacuo to yield the title compound as a solid.

$^1$H NMR (300 MHz, CDCl$_3$) δ 7.30-7.25 (2H, m), 7.09-7.04 (1H,m), 6.96-6.93 (1H, m), 3.89-3.85 (4H, m), 3.82-3.79 (4H, m), 2.6 (br s, 1H), 1.86-1.76 (4H, m), 1.50 (s, 9H)

MS (ES$^+$) m/z 369.2 (M+H)$^+$

EXAMPLE 91

Production of Cells Expressing the ORL-1, Delta, Kappa or Mu Receptor

HEK293 cells were transfected with nociceptin receptor (ORL-1, human mRNA GenBank #AF348323) or any of the opioid receptor subtype delta (δ, human mRNA Genbank

U07882) kappa (κ, human mRNA Genbank #U17298) and mu (μ, human mRNA Genbank #L29301). The vector used was pCi-neo (G418 selection). The transfections were performed with LipofectAMINE 2000 (Life Technologies Cat. #11668-019) using the following procedure.

The day before transfection, a 24 well plate was inoculated with $2\times10^5$ cells per well in 0.5 ml of normal growth medium (MEM+EBSS+NEAA+10% BCS). Two wells were prepared for each specialty along with a no DNA control. For each well transfected, 0.8 μg of DNA was diluted into 5011 (total volume) of OPTI-MEM I Reduced Serum Medium (Life Technologies Cat. #51985-034). For each well transfected, 2 μl of LipofectAMINE 2000 (LF2000) was diluted into 50 μl (total volume) of OPTI-MEM I medium and incubated for 5 minutes at room temperature. The diluted DNA and LF2000 were combined and incubated at room temperature for 20 minutes. The growth medium was aspirated from each well and replaced with 1 ml of OPTI-MEM I. A total of 100 μl of the DNA-LF2000 complexes were added to each well and mixed with gentle swirling. The plate was incubated at 37° C., 5% $CO_2$ for 5 hours. The OPTI-MEM I medium was aspirated from each transfected well and replaced with 1 ml growth medium. The plate was returned to the incubator for 24 hours. The wells were trypsinized and cells added to 100 mm tissue culture dishes (2 dishes per well). The dishes were incubated for 24 hours. The medium was aspirated from each dish and replaced with growth medium containing 400 g/ml Geneticin (G418) selective antibiotic. The plates were refer every 3-4 days.

Distinct colonies appeared in approximately 3 weeks. One week later, 48 out of approximately 100 colonies per dish were subcultures to 1 well each of two 24 well plates containing 1 ml of selective medium per well.

Confluent wells were expanded to 6 well plates, then T25 flasks and T75 flasks. Cell lines showing poor growth patterns were eliminated. Membranes were prepared from each cell line and receptor activity determined by a receptor binding assay.

EXAMPLE 92

Assay to Measure Affinity for the ORL-1 Receptor

The nociceptin receptor binding assay measures the binding of $^{125}$I-Tyr$^{14}$-nociceptin (2200 Ci/mmol, New England Nuclear) to human nociceptin receptor (ORL-1) on HEK293 cell membranes.

HEK293 cell membrane (prepared as described in Pulito, V. L. et al., 2000, *J. Pharmacol. Exp. Ther.* 294, 224-229), with the exception that the buffer used was a mixture of 50 mM Tris-HCl pH7.8, 5 mM $MgCl_2$ and 1 mM EGTA), was added to PEI treated WGA FlashPlates (New England Nuclear) at 1 μg/well in binding buffer of 50 mM Tris-HCl pH 7.8, 5 mM $MgCl_2$ and 1 mM EGTA. $^{125}$I-Tyr$^{14}$-nociceptin was added at a final concentration of 0.5 nM and the volume adjusted to 50 μl with binding buffer. The plate was incubated for two hours at room temperature, the reactions were aspirated and the wells washed two times with 200 μl binding buffer and then filled with 200 μl binding buffer. The plates were then sealed and counted on a Packard Top Count to determine radioactivity bound to the membranes.

For each test compound, the total binding (% Inh) was measured at several concentrations and the $IC_{50}$ (the concentration at which 50% of the binding is inhibited) was deter-mined from the graphical display of X=logarithm of concentration versus Y=response, using the following calculation:

$$Y = (\text{Minimum}) + \frac{(\text{Maximum} - \text{Minimum})}{(1 + 10^{\log(EC_{50} - X)})}$$

The ability of representative compounds of the present invention to bind to the ORL-1 receptor in a HEK cell line using a radio-labeled nociceptin as the displaceable ligand was determine according to the procedure described above with results as listed in Table 3. (Note that for the compounds which were tested more than once, the value listed in Table 3 is the calculated mean.)

TABLE 3

| Compound # | $IC_{50}$ (μM) |
|---|---|
| 1 | 0.51 |
| 2 | >10 |
| 3 | 0.68 |
| 4 | >10 |
| 5 | >10 |
| 7 | 7.40 |
| 8 | 0.60 |
| 9 | 0.023 |
| 11 | 0.88 |
| 12 | 0.14 |
| 13 | >10 |
| 14 | >10 |
| 15 | 0.90 |
| 16 | 0.11 |
| 17 | >10 |
| 18 | 0.38 |
| 19 | 2.68 |
| 20 | 0.29 |
| 21 | 1.31 |
| 22 | >10 |
| 23 | 3.6 |
| 24 | 0.80 |
| 25 | 1.08 |
| 26 | 0.82 |
| 27 | 1.12 |
| 28 | >10 |
| 29 | 0.10 |
| 30 | 0.35 |
| 31 | >10 |
| 32 | 0.25 |
| 35 | 2.4 |
| 37 | >10 |
| 39 | 0.71 |
| 40 | >10 |
| 41 | >10 |
| 42 | 0.10 |
| 43 | 0.47 |
| 44 | 0.12 |
| 45 | 0.032 |
| 46 | 0.18 |
| 55 | 2.75 |
| 57 | 0.45 |
| 58 | 0.15 |
| 59 | 0.037 |
| 60 | 0.083 |
| 61 | 0.12 |
| 62 | 0.32 |
| 63 | 3.37 |

EXAMPLE 93

Filtration Binding Assay: Mu, Kappa and Delta Opioid Receptors

The assay used to measure the binding of representative test compounds to the ORL-1, delta, kappa and mu opioid receptors were similarly run, with appropriate selection and substitution of cell membrane and radiolabeled ligand. The following cell membranes and ligands were used for the determination of binding to the respective opioid receptors.

Delta (δ) opioid: 5 μg/well of 2D4 cell line membrane DPDPE-H³ ligand at a ration of 1:1000.
Mu (μ) opioid: with 10 μg/well of 1 D4 cell line membrane Damgo-H³ ligand at a ration of 1:1000.
Kappa (κ) opioid: 5 μg/well of 2C2 cell line membrane U69593-H3 ligand at a ration of 1:1000.

Both membrane and ligand were diluted such that a 25 μl addition delivered the necessary amount per well, as noted above. Both membrane and ligand were diluted in 1× ORL-1 buffer. The ORL-1 buffer was a mixture of 50 mM Tris-HCl, pH=7.4, 5 mM $MgCl_2$ and 1 mM EGTA. Each test compound was diluted to a concentration in the range of from 100 μM to 10 pM with 100% DMSO. To each well of a 96 well plate was added 1 μL of the diluted test compound, 25 μL cell membrane (as listed above) and 25 μL labeled ligand (as listed above) for the mu, delta, kappa or ORL-1 opioid receptor, as desired.

The plate was incubated on a rotating shaker for 2 hours at room temperature. The plate was filtered over GF/C Filter-plates, prewetted in 0.03% polyethleneimine, in Filtermate 196 apparatus (Packard). The plate was then washed 6 times with ORL-1 buffer in the filtration apparatus and dried in vacuum oven for 1 hour at a temperature of 50° C.

To each well was then added 25 μL Microscint 20 (Packard) (to solubilize bound radioactivity) and each well counted in a Packard TopCount for 1 minute/well using counting parameters optimized for the particular radioligand/opioid receptor being tested. Percent radioactive ligand bound in each reaction was calculated relative to a control using DMSO for maximum binding (no inhibition). Curves were fitted and $IC_{50}$s determined using Graphpad Prizm software (v3.0).

Representative compounds of the present invention were tested for binding to the mu, kappa and delta opioid receptors using the procedure, cell membranes and ligands as described above, with results as listed in Table 4. (Note that for the compounds which were tested more than once, the value listed in Table 4 is the calculated mean.)

TABLE 4

| Compound # | Delta (δ) $IC_{50}$ (μM) | Mu (μ) $IC_{50}$ (μM) | Kappa (κ) $IC_{50}$ (μM) |
|---|---|---|---|
| 4 | >10 | >10 | |
| 5 | >10 | >10 | >10 |
| 7 | >10 | 0.98 | 0.097 |
| 8 | >10 | 5.31 | |
| 9 | >10 | 1.01 | 0.25 |
| 16 | >10 | 0.36 | 0.36 |
| 17 | 5.7 | >10 | 4.00 |
| 18 | >10 | 1.11 | 0.43 |
| 19 | 0.30 | >10 | 0.12 |
| 20 | | 1.69 | |
| 30 | >10 | >10 | 4.41 |
| 35 | >10 | 1.61 | 1.22 |
| 41 | >10 | >10 | >10 |
| 42 | >10 | 3.55 | 0.64 |
| 44 | >10 | 0.96 | 1.10 |
| 45 | >10 | 1.30 | 0.93 |
| 46 | >10 | 1.41 | 2.64 |
| 55 | >10 | 1.46 | |
| 57 | >10 | 4.28 | 0.54 |
| 58 | 8.80 | 6.47 | 2.38 |
| 59 | >10 | 0.48 | 0.56 |
| 60 | >10 | 0.84 | 0.48 |
| 61 | >10 | 0.50 | 0.10 |
| 62 | >10 | 0.62 | 0.22 |
| 63 | >10 | >10 | >10 |

EXAMPLE 94

ORL-1 Functional Assay

To assay the function of a test compound, a HEK-293 cell line that over-expresses the ORL-1 receptor and the Gqi5 G protein (Molecular Devices) were employed. By using a calcium flux assay, agonism and antagonism through the ORL-1 receptor were detectable.

The HEK-293 cells were plated two days prior to assay. For assay, cells in 50 μl of medium were incubated with 50 μl of dye (Molecular Devices) for 1 hour at 37° C. 100 μl of test compound diluted in Hank's Buffered Salt Solution (HBSS) at 2-fold the indicated final concentration was added and time points taken every 1 second for 1 minute and every 3 seconds for an additional 1 minute using FLIPR384 (Molecular Devices). 50 μl of nociceptin (Neosystems, SA) at 5-fold the indicated final concentration was then added and additional time points were recorded every 1 second for 1 minute and every 3 seconds for an additional 1 minute.

The resulting data were processed using Microsoft Excel 6.0 and $EC_{50}$ values were determined using GraphPad Prism 3.0. For agonists, the $EC_{50}$ was determined from the initial calcium signal obtained after addition of the test compound. For compounds that behaved as antagonists, the percent inhibition or $IC_{50}$ of the signal resulting from the subsequent addition of the nociceptin peptide was calculated.

Representative compounds of the present invention were tested according to the procedure described above, as listed in Table 5 below. In the column titled "Inhibitor" a notation of "no" indicates that the compound did not act as an inhibitor, a notation of "yes" indicates that the compound acted as an inhibitor and a notation of "undetermined" indicates that the data did not clearly show whether or not the compound acted as an antagonist.

TABLE 5

| Compound # | Inhibitor | % Inhibition (100 nM Nociceptin) |
|---|---|---|
| 1 | no | — |
| 9 | undetermined | 41 ± 26 |
| 18 | yes | 45 ± 9 |
| 24 | yes | 32 ± 2 |
| 45 | no | — |
| 46 | no | — |
| 57 | no | — |
| 58 | undetermined | 48 ± 26 |
| 59 | yes | 81 ± 6 |
| 60 | no | 17 ± 3 |

EXAMPLE 95

As a specific embodiment of an oral composition, 100 mg of the Compound #9, prepared as in Example 63 is formulated with sufficient finely divided lactose to provide a total amount of 580 to 590 mg to fill a size 0 hard gel capsule.

While the forgoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

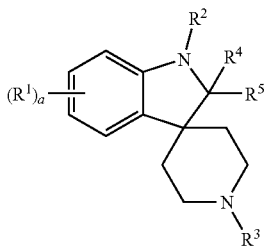

wherein
a is an integer from 0 to 1;
R¹ is selected from the group consisting of 9-fluoro and 8-methyl;
R² is selected from the group consisting of methyl and oxarinayl-methyl-;
R³ is cyclooctyl-methyl-;
R⁴ and R⁵ are taken together as =O;
or a pharmaceutically acceptable salt thereof.

2. A pharmaceutical composition comprising a pharmaceutically acceptable carrier and a compound of claim 1.

3. A pharmaceutical composition made by mixing a compound of claim 1 and a pharmaceutically acceptable carrier.

4. A process for making a pharmaceutical composition comprising mixing a compound of claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,655,670 B2 |
| APPLICATION NO. | : 11/440731 |
| DATED | : February 2, 2010 |
| INVENTOR(S) | : Battista et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 721 days.

Signed and Sealed this

Twenty-third Day of November, 2010

David J. Kappos
*Director of the United States Patent and Trademark Office*